(12) United States Patent
Roe

(10) Patent No.: US 9,486,164 B2
(45) Date of Patent: *Nov. 8, 2016

(54) HANDHELD MEDICAL DIAGNOSTIC DEVICE WITH LANCET AND SAMPLE TRANSFER

(71) Applicant: Roche Diabetes Care, Inc., Indianapolis, IN (US)

(72) Inventor: Steven N Roe, San Mateo, CA (US)

(73) Assignee: Roche Diabetes Care, Inc., Indianapolis, IN (US)

(*) Notice: Subject to any disclaimer, the term of this patent is extended or adjusted under 35 U.S.C. 154(b) by 85 days.

This patent is subject to a terminal disclaimer.

(21) Appl. No.: 14/473,015

(22) Filed: Aug. 29, 2014

(65) Prior Publication Data
US 2014/0371630 A1  Dec. 18, 2014

Related U.S. Application Data

(63) Continuation of application No. 12/981,871, filed on Dec. 30, 2010, now Pat. No. 8,158,428.

(51) Int. Cl.
*G01N 33/58* (2006.01)
*A61B 5/151* (2006.01)
(Continued)

(52) U.S. Cl.
CPC ....... *A61B 5/15117* (2013.01); *A61B 5/14532* (2013.01); *A61B 5/157* (2013.01); *A61B 5/15128* (2013.01); *A61B 5/15192* (2013.01); *A61B 5/150229* (2013.01);
(Continued)

(58) Field of Classification Search
CPC .................................................... G01N 33/58

USPC .................... 436/93–95, 174; 600/583–584
See application file for complete search history.

(56) References Cited

U.S. PATENT DOCUMENTS 4,794,926 A   1/1989 Munsch et al.
5,029,583 A   7/1991 Meserol et al.
(Continued)

FOREIGN PATENT DOCUMENTS

CN   1456887 A1   11/2003
EP   1203563 A2   10/2001
(Continued)

OTHER PUBLICATIONS

International Search Report, Appln. No. PCT/EP2011/072891, Mar. 7, 2012.
(Continued)

*Primary Examiner* — Arlen Soderquist
(74) *Attorney, Agent, or Firm* — Roche Diabetes Care, Inc.

(57) ABSTRACT

A lancet housing assembly for use in a portable handheld medical diagnostic device for sampling bodily fluids from a skin site of a patient is provided. The lancet housing assembly comprises an outer facing side and an inner facing side. An opening is located at the outer facing side that is arranged and configured to align with a lancet port of the medical diagnostic device. A floor extends between the outer facing side and the inner facing side and having a reagent material. A lancet structure having a skin penetrating end and a blood transport portion adjacent the skin penetrating end is located in housing assembly. The blood transport portion is arranged and configured receive the amount of blood from the skin penetrating end and to carry the amount of blood away from the skin site and to the reagent material.

18 Claims, 34 Drawing Sheets

(51) Int. Cl.
*G01N 25/72* (2006.01)
*A61B 5/145* (2006.01)
*A61B 5/15* (2006.01)
*A61B 5/157* (2006.01)
*A61B 5/00* (2006.01)
*F01D 21/00* (2006.01)
*G01M 15/14* (2006.01)
*F01D 9/02* (2006.01)
*G01N 21/84* (2006.01)
*F01D 17/08* (2006.01)

(52) U.S. Cl.
CPC .............. *A61B 5/742* (2013.01); *F01D 9/023* (2013.01); *F01D 21/003* (2013.01); *G01M 15/14* (2013.01); *G01N 25/72* (2013.01); *F01D 17/085* (2013.01); *F05D 2260/80* (2013.01); *F05D 2260/83* (2013.01); *G01N 21/8422* (2013.01); *Y02T 50/675* (2013.01)

(56) References Cited

U.S. PATENT DOCUMENTS

| | | | |
|---|---|---|---|
| 5,829,589 A | 11/1998 | Nguyen et al. | |
| 6,228,100 B1 | 5/2001 | Schraga | |
| 6,616,616 B2 | 9/2003 | Fritz et al. | |
| 6,706,159 B2 | 3/2004 | Moerman et al. | |
| 7,004,928 B2 | 2/2006 | Aceti et al. | |
| 7,025,774 B2 | 4/2006 | Freeman et al. | |
| 7,141,058 B2 | 11/2006 | Briggs et al. | |
| 7,150,755 B2 | 12/2006 | Levaughn et al. | |
| 7,175,642 B2 | 2/2007 | Briggs et al. | |
| 7,192,405 B2 | 3/2007 | DeNuzzio et al. | |
| 7,198,606 B2 | 4/2007 | Boecker et al. | |
| 7,223,248 B2 | 5/2007 | Erickson et al. | |
| 7,226,461 B2 | 6/2007 | Boecker et al. | |
| 7,258,693 B2 | 8/2007 | Freeman et al. | |
| 7,297,151 B2 | 11/2007 | Boecker et al. | |
| 7,343,188 B2 | 3/2008 | Sohrab | |
| 7,344,507 B2 | 3/2008 | Briggs et al. | |
| 7,374,544 B2 | 5/2008 | Freeman et al. | |
| 7,377,904 B2 | 5/2008 | Conway et al. | |
| 7,481,776 B2 | 1/2009 | Boecker et al. | |
| 7,491,178 B2 | 2/2009 | Boecker et al. | |
| 7,524,293 B2 * | 4/2009 | Freeman | A61B 5/1411 600/573 |
| 7,582,063 B2 | 9/2009 | Wurster et al. | |
| 7,604,592 B2 | 10/2009 | Freeman et al. | |
| 7,708,701 B2 | 5/2010 | Boecker et al. | |
| 7,713,214 B2 | 5/2010 | Freeman et al. | |
| 7,771,367 B2 | 8/2010 | Haar et al. | |
| 7,798,979 B2 * | 9/2010 | Freeman | A61B 5/1411 600/573 |
| 7,837,633 B2 | 11/2010 | Conway et al. | |
| 7,842,060 B2 | 11/2010 | List | |
| 7,875,047 B2 | 1/2011 | Freeman et al. | |
| 7,892,183 B2 | 2/2011 | Boecker et al. | |
| 7,892,185 B2 | 2/2011 | Freeman et al. | |
| 8,852,123 B2 * | 10/2014 | Roe | 600/583 |
| 2002/0052618 A1 | 5/2002 | Haar et al. | |
| 2002/0188224 A1 | 12/2002 | Roe et al. | |
| 2003/0199896 A1 * | 10/2003 | Boecker | A61B 5/1411 606/181 |
| 2003/0211619 A1 | 11/2003 | Olson et al. | |
| 2003/0212345 A1 | 11/2003 | McAllister et al. | |
| 2003/0212347 A1 | 11/2003 | Sohrab | |
| 2004/0064068 A1 * | 4/2004 | DeNuzzio | A61B 5/1411 600/583 |
| 2004/0138588 A1 | 7/2004 | Saikley et al. | |
| 2004/0193202 A1 | 9/2004 | Allen | |
| 2005/0154410 A1 | 7/2005 | Conway et al. | |
| 2006/0020228 A1 | 1/2006 | Fowler et al. | |
| 2006/0064035 A1 | 3/2006 | Wang et al. | |
| 2006/0094985 A1 | 5/2006 | Aceti et al. | |
| 2006/0157362 A1 * | 7/2006 | Schraga | A61B 5/1411 206/363 |
| 2006/0178600 A1 | 8/2006 | Kennedy et al. | |
| 2006/0200044 A1 | 9/2006 | Freeman et al. | |
| 2006/0204399 A1 | 9/2006 | Freeman et al. | |
| 2006/0241517 A1 * | 10/2006 | Fowler | A61B 5/1411 600/583 |
| 2006/0241666 A1 | 10/2006 | Briggs et al. | |
| 2006/0241667 A1 | 10/2006 | Freeman | |
| 2007/0038235 A1 * | 2/2007 | Freeman | A61B 5/1411 606/181 |
| 2007/0055174 A1 * | 3/2007 | Freeman | A61B 5/1411 600/583 |
| 2007/0100255 A1 | 5/2007 | Boecker et al. | |
| 2007/0100256 A1 | 5/2007 | Sansom | |
| 2007/0123802 A1 * | 5/2007 | Freeman | A61B 5/1411 600/583 |
| 2007/0129650 A1 | 6/2007 | Freeman et al. | |
| 2007/0142748 A1 | 6/2007 | Deshmukh et al. | |
| 2007/0173741 A1 | 7/2007 | Deshmukh et al. | |
| 2007/0179406 A1 | 8/2007 | DeNuzzio et al. | |
| 2007/0219574 A1 | 9/2007 | Freeman et al. | |
| 2008/0009768 A1 | 1/2008 | Sohrab | |
| 2008/0009892 A1 | 1/2008 | Freeman et al. | |
| 2008/0021492 A1 | 1/2008 | Freeman et al. | |
| 2008/0208078 A1 * | 8/2008 | Neel | A61B 5/1411 600/583 |
| 2008/0269791 A1 | 10/2008 | Hoenes et al. | |
| 2008/0300614 A1 | 12/2008 | Freeman et al. | |
| 2009/0048536 A1 | 2/2009 | Freeman et al. | |
| 2009/0099477 A1 | 4/2009 | Hoenes et al. | |
| 2009/0099585 A1 | 4/2009 | Conway et al. | |
| 2009/0270765 A1 | 10/2009 | Ghesquiere et al. | |
| 2010/0015692 A1 * | 1/2010 | Feldman | C12Q 1/001 435/288.7 |
| 2010/0049234 A1 | 2/2010 | Kitamura et al. | |
| 2010/0057119 A1 | 3/2010 | Robbins et al. | |
| 2010/0125294 A1 | 5/2010 | Yasui | |
| 2010/0145229 A1 * | 6/2010 | Perez | A61B 5/1411 600/583 |
| 2010/0145377 A1 | 6/2010 | Lai et al. | |
| 2010/0174211 A1 | 7/2010 | Frey et al. | |
| 2010/0204612 A1 | 8/2010 | Choi et al. | |
| 2010/0234869 A1 | 9/2010 | Sacherer | |
| 2010/0312266 A1 | 12/2010 | Fukuzawa | |
| 2011/0015661 A1 | 1/2011 | Keil | |
| 2012/0039772 A1 | 2/2012 | Hoenes | |

FOREIGN PATENT DOCUMENTS

| | | |
|---|---|---|
| EP | 1 360 935 A1 | 5/2003 |
| EP | 1 402 812 A1 | 9/2003 |
| EP | 1 360 934 A1 | 11/2003 |
| EP | 1 508 304 A1 | 2/2005 |
| EP | 1 847 219 A1 | 10/2007 |
| EP | 2042098 A1 | 4/2009 |
| EP | 2 113 197 A1 | 11/2009 |
| EP | 2226007 A1 | 9/2010 |
| EP | 2 236 082 A1 | 10/2010 |
| WO | 2003/070099 A1 | 8/2003 |
| WO | 2007/019202 A2 | 2/2004 |
| WO | 2005/006939 A2 | 1/2005 |
| WO | 2005/016125 A2 | 2/2005 |
| WO | 2005/033659 A2 | 4/2005 |
| WO | 2005/065415 A2 | 7/2005 |
| WO | 2005/121759 A2 | 12/2005 |
| WO | 2007/021979 A2 | 2/2007 |
| WO | 2007/060004 A1 | 5/2007 |
| WO | 2007/084367 A2 | 7/2007 |
| WO | 2009/037192 A1 | 3/2009 |
| WO | 2009/075907 A2 | 6/2009 |
| WO | 2010/064998 A1 | 6/2010 |

(56) References Cited

FOREIGN PATENT DOCUMENTS

| WO | 2011/044971 | 4/2011 |
|----|-------------|--------|
| WO | 2011044971 A2 | 4/2011 |

OTHER PUBLICATIONS

International Search Report and Written Opinion completed Mar. 1, 2012 pertaining to International Application No. PCT/EP2011/072893.

International Search Report, PCT Application PCT/EP2011/072885, Filed Dec. 15, 2011, 6 pages.

European Patent Office Search Report and Written Opinion mailed Mar. 7, 2012 in reference to co-pending European Patent Application No. PCT/EP2011/072893 filed Dec. 15, 2011.

European Patent Office International Preliminary Report on Patentability mailed Feb. 18, 2013 in reference to co-pending European Patent Application No. PCT/EP2011/072893 filed Dec. 15, 2011.

Office Action mailed Jun. 14, 2013 from U.S. Appl. No. 12/981,811, filed Dec. 30, 2010.

Office Action mailed Jun. 13, 2013 from U.S. Appl. No. 12/981,816, filed Dec. 30, 2010.

Office Action mailed Jun. 20, 2013 from U.S. Appl. No. 12/981,677, filed Dec. 30, 2010.

Office Action mailed Jun. 13, 2013 from U.S. Appl. No. 12/981,696, filed Dec. 30, 2010.

\* cited by examiner

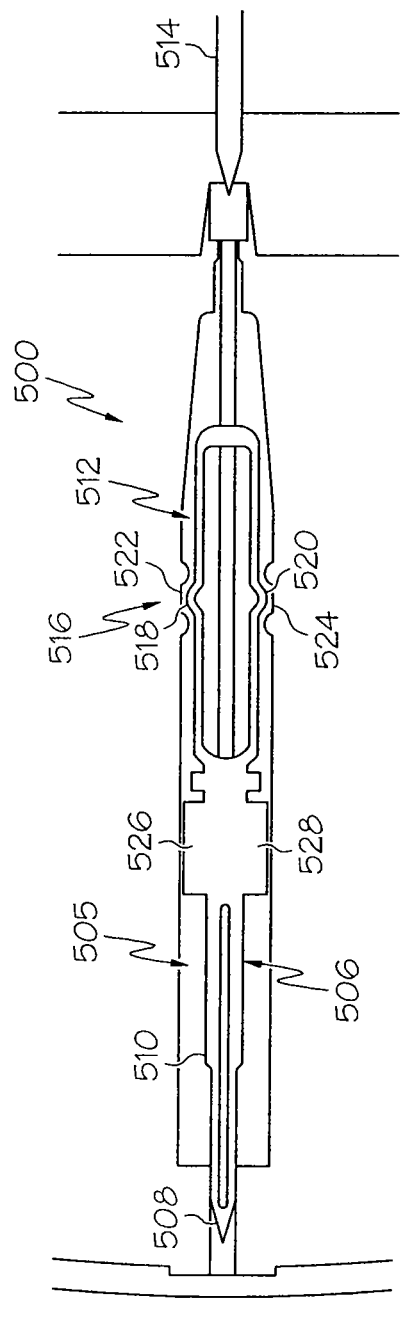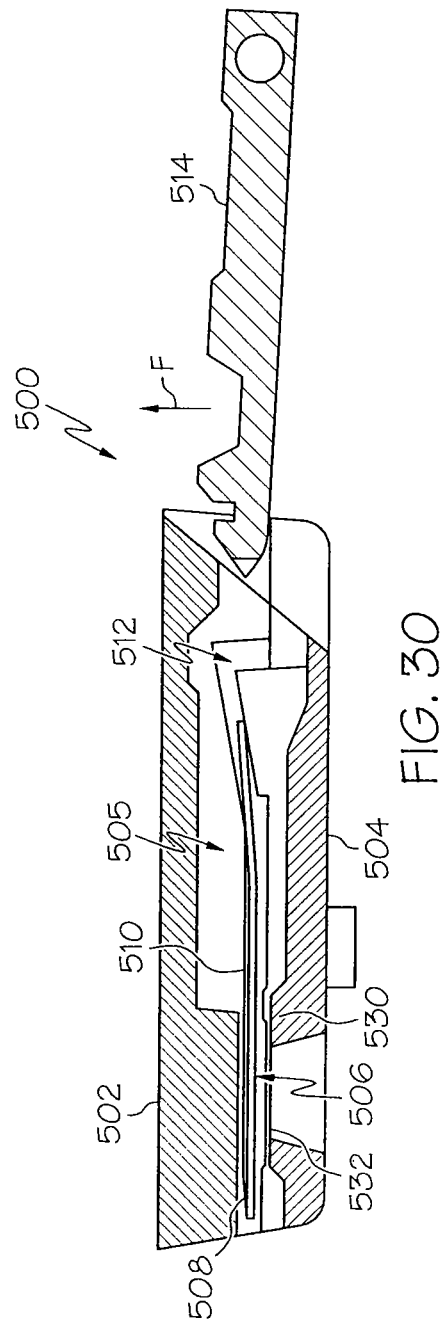

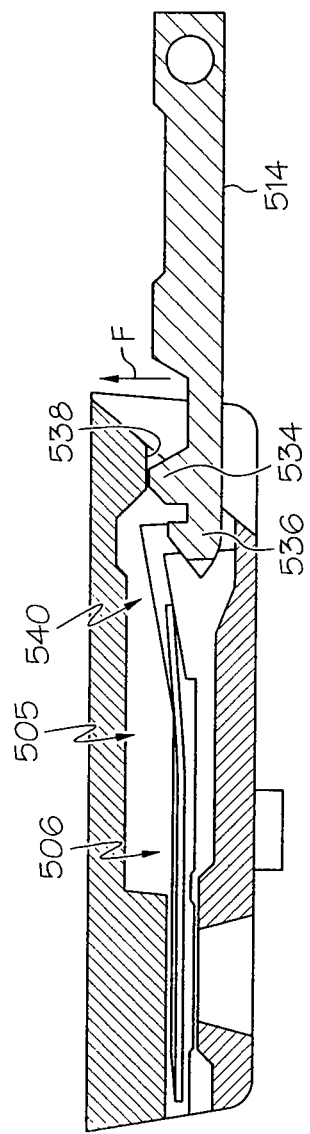
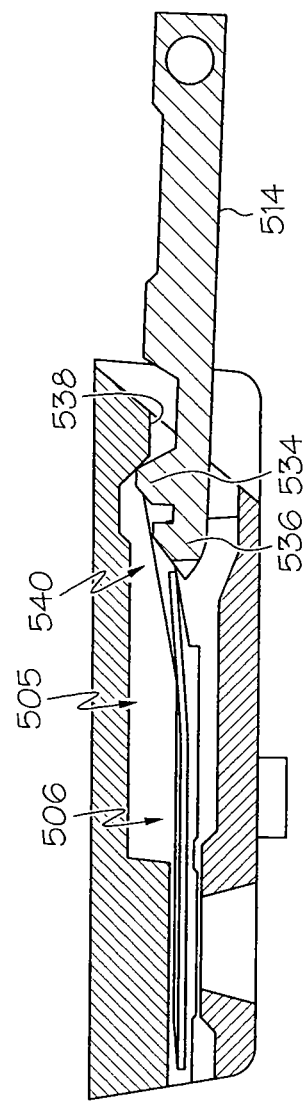

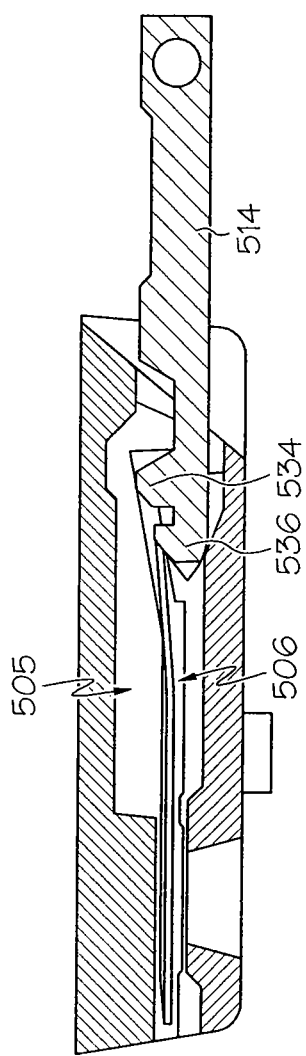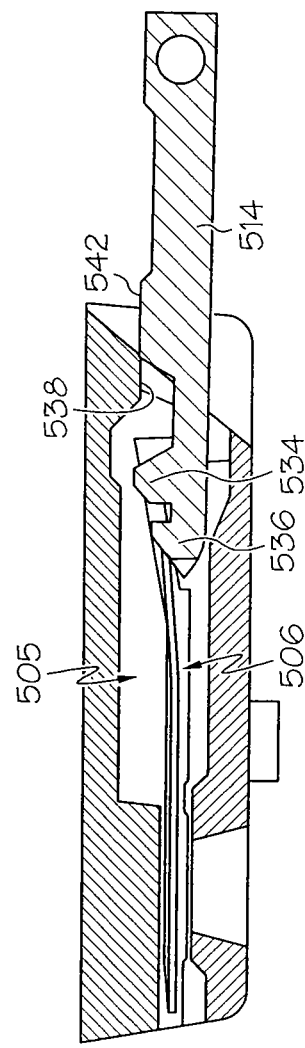

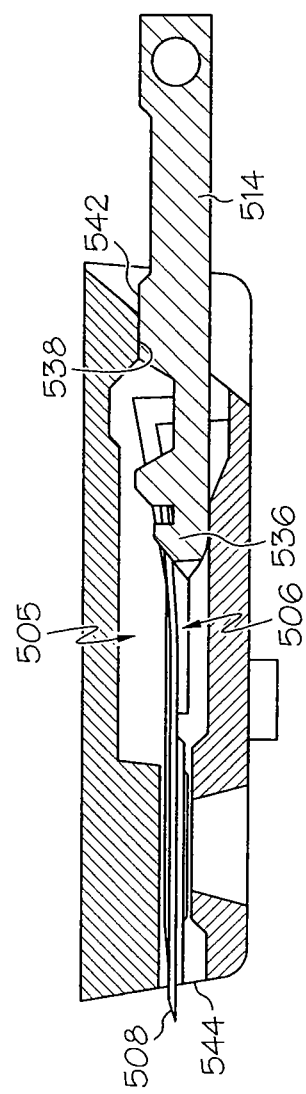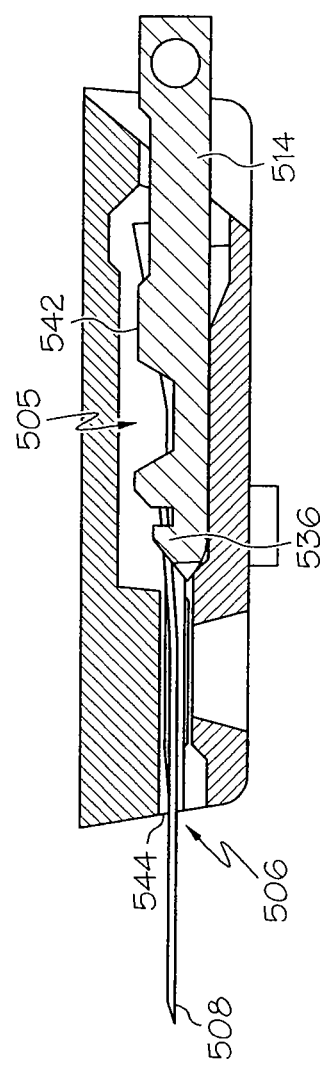

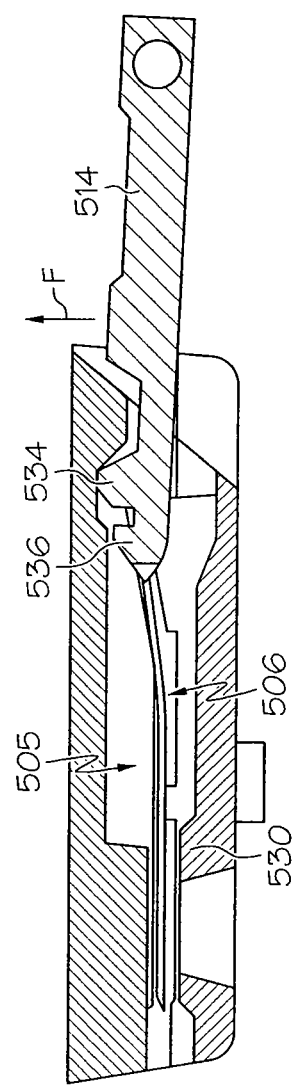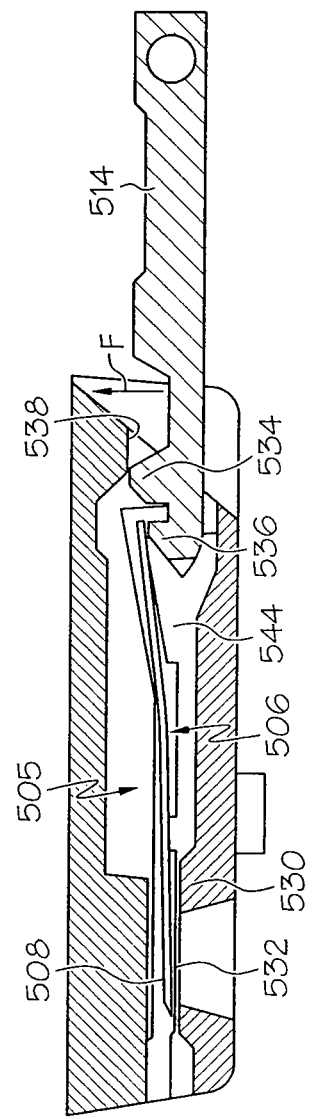

HANDHELD MEDICAL DIAGNOSTIC DEVICE WITH LANCET AND SAMPLE TRANSFER

CROSS-REFERENCE TO RELATED APPLICATIONS

The present patent application is a continuation of U.S. patent application Ser. No. 12/981,781, filed on Dec. 30, 2010 (now U.S. Pat. No. 8,852,123; issued on Oct. 7, 2014), which is incorporated herein by reference as if set forth in its entirety.

TECHNICAL FIELD

The present disclosure relates generally to handheld medical devices, and in particular, to a handheld medical diagnostic device that can reduce steps needed to measure concentrations of biologically significant components of bodily fluids.

BACKGROUND

Portable handheld medical diagnostic devices are often employed to measure concentrations of biologically significant components of bodily fluids, such as, for example, glucose concentration in blood. The portable handheld medical diagnostic devices and their accessories may work together to measure the amount of glucose in blood and be used to monitor blood glucose in one's home, healthcare facility or other location, for example, by persons having diabetes or by a healthcare professional.

For people with diabetes, regular testing of blood glucose level can be an important part of diabetes management. Thus, it is desirable to provide medical diagnostic devices that are portable and easy to use. Various medical diagnostic devices have been introduced for testing blood sugar that are portable. However, there continues to be a need for improved portability and ease of use for medical diagnostic devices.

Often times, self-monitoring of blood glucose may require the patient to first load a lancet into a lancer and a separate test strip into a blood glucose meter. The lancer and lancet are then used to prick the finger and a small drop of blood is squeezed to the surface. The sample port on the strip is brought into contact with the blood and the sample may be transported to the reaction zone on the strip. This can be a labor-intensive, uncomfortable process that requires multiple steps and devices. Patients may need to repeat this process several times a day.

SUMMARY

In one embodiment, a lancet housing assembly comprising multiple lancets for use in a portable handheld medical diagnostic device for sampling bodily fluids from a skin site of a patient is provided. The lancet housing assembly includes a housing structure comprising multiple lancet compartments. At least one of the lancet compartments comprises an outer facing side and an inner facing side. An opening is located at the outer facing side that is arranged and configured to align with a lancet port of the medical diagnostic device. A floor extends between the outer facing side and the inner facing side. A reagent material is located on the floor and within the lancet compartment. A lancet structure is located in the at least one lancet compartment. The lancet structure comprises a skin penetrating end and a blood transport portion adjacent the skin penetrating end. The skin penetrating end, when extended through the opening, is shaped and sized to penetrate the patient's skin at the skin site to provide an amount of blood. The blood transport portion is arranged and configured receive the amount of blood from the skin penetrating end and to carry the amount of blood away from the skin site and to the reagent material.

In another embodiment, a portable handheld medical diagnostic device for sampling bodily fluids includes a protective enclosure. A measurement system includes a controller facilitating a physiologic measurement. A display device is connected to the measurement system that displays information related to the physiologic measurement. A housing structure comprises multiple lancet compartments. At least one of the lancet compartments includes an outer facing side and an inner facing side. An opening is located at the outer facing side that is arranged and configured to align with a lancet port of the medical diagnostic device. A floor extends between the outer facing side and the inner facing side. A reagent material is located on the floor and within the lancet compartment. A lancet structure is located in the at least one lancet compartment. The lancet structure comprises a skin penetrating end and a blood transport portion adjacent the skin penetrating end. The skin penetrating end, when extended through the opening, is shaped and sized to penetrate the patient's skin at the skin site to provide an amount of blood. The blood transport portion is arranged and configured receive the amount of blood from the skin penetrating end and to carry the amount of blood away from the skin site and to the reagent material.

In another embodiment, a method of controlling movement of one or more lancet structures provided within a lancet housing assembly in a portable handheld medical diagnostic device for sampling bodily fluids from a skin site of a patient is provided. The method includes locating a lancet structure in at least one lancet compartment of the lancet housing assembly. The lancet structure includes a skin penetrating end and a blood transport portion adjacent the skin penetrating end. The skin penetrating end is extended through a port of the medical diagnostic device and penetrating the patient's skin at the skin site to provide an amount of blood. The amount of blood is received at the skin penetrating end. The amount of blood is carried away from the skin site using the blood transport portion to the reagent material.

These and other advantages and features of the various embodiments of the invention disclosed herein, will be made more apparent from the description, drawings and claims that follow.

BRIEF DESCRIPTION OF THE DRAWINGS

The following detailed description of the exemplary embodiments of the present invention can be best understood when read in conjunction with the following drawings, where like structure is indicated with like reference numerals, and in which:

FIG. 29 illustrates another embodiment of lancet housing assembly;

FIG. 30 illustrates the lancet housing assembly of FIG. 29 in operation;

FIG. 31 illustrates the lancet housing assembly of FIG. 29 in operation;

FIG. 32 illustrates the lancet housing assembly of FIG. 29 in operation;

FIG. 33 illustrates the lancet housing assembly of FIG. 29 in operation;

FIG. 34 illustrates the lancet housing assembly of FIG. 29 in operation;

FIG. 35 illustrates the lancet housing assembly of FIG. 29 in operation;

FIG. 36 illustrates the lancet housing assembly of FIG. 29 in operation;

FIG. 37 illustrates the lancet housing assembly of FIG. 29 in operation;

FIG. 38 illustrates the lancet housing assembly of FIG. 29 in operation;

DETAILED DESCRIPTION

The following description of the preferred embodiment is merely exemplary in nature and is in no way intended to limit the invention or its application or uses.

Embodiments described herein generally relate to handheld medical diagnostic devices that are used to acquire and measure concentrations of biologically significant components of bodily fluids. In particular, the handheld medical diagnostic device may be used to acquire a blood sample and measure a blood glucose level of the sample. As will be described below, the medical diagnostic device may include a motor-driven lancet structure inside the medical diagnostic device, which can be used to generate a prick wound in a body part. The lancet structure can also be used to take up blood emerging from the prick wound using capillary action and deliver the blood to a reagent material. A measuring system located in the medical diagnostic device may be used to determine a blood glucose concentration value of the acquired blood.

Figure 1:
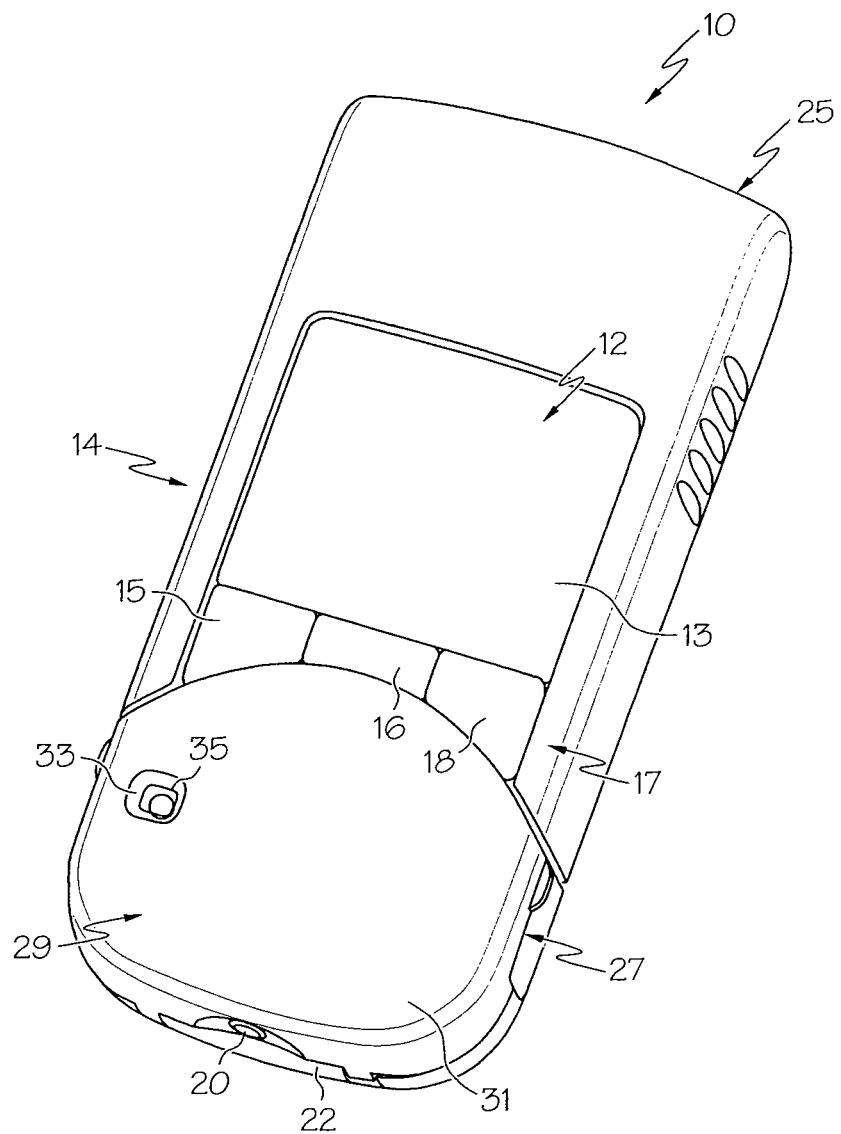
FIG. 1 is a perspective view of an embodiment of a portable handheld medical diagnostic device.

Referring to FIG. 1, a portable, handheld medical diagnostic device 10 with a display device 12 behind a transparent, protective lens 13 includes a protective enclosure, generally indicated by element 14 that protects electronics and other mechanical components therein. The protective enclosure 14 is somewhat rectangular in shape, however, any other suitable shapes may be used for the protective enclosure, such as circular shapes, etc. The display device 12 may be any suitable display device used in a portable, handheld electronic device, such as, for example, but not limited to LCD display devices, LED display devices, OLED display devices, and other types of display devices which may be heretofore developed. Further, display device 12 may be any other variety of indicators, including, but not limited to a series of lights and/or other types of light devices as opposed to a single integrated display screen. In the illustrated embodiment, the display device 12 includes an electronic paper component such as an electrophoretic display, which may be an information display that forms visible images by rearranging charged pigment particles using an electric field. The display device 12 may be used for electronically displaying graphics, text, and other elements to a user. In some embodiments, the display device 12 may be a touch-screen user interface that is used with the tip of a finger of the user and/or a stylus or other touching device to select elements from the screen, to draw figures, and to enter text with a character recognition program running on the device 10. In some embodiments, the medical diagnostic device 10 may also include other types of output devices such as for example, sound devices, vibration devices, etc.

The medical diagnostic device 10 further includes a user interface (generally referred to as element 17), which may include buttons 15, 16 and 18. The buttons 15, 16 and 18 may be used by an operator, for example, to view memory of the medical diagnostic device 10, adjust settings of the device and scroll through test results. The buttons 15, 16 and 18 may be manually actuated, such as by pressing the buttons. The buttons 15, 16 and 18 may comprise touch sensors (e.g., resistive or capacitive touch sensors, surface acoustic wave sensors, infrared LED, photodetectors, piezoelectric transducers, etc.) that can be actuated by placing and/or pressing a tip of the finger within the button areas. In these embodiments, the buttons 15, 16 and 18 may not move. Instead, the buttons 15, 16 and 18 may be indicated visually to identify where to place the finger. In other embodiments utilizing touch sensors, the buttons 15, 16 and 18 may move, for example, to bring the finger or touching device into close proximity to the touch sensor. In some embodiments, the medical diagnostic device 10 may provide other button or input types such as an OK button and/or joy stick/track ball, which a user may utilize to navigate through a software drive menu provided on the display device 12. Additional buttons may be used as shortcut buttons, for example, to call up a certain program on the medical diagnostic device 10, as a method of scrolling, to select items from a list, or to provide any function that the software designer of the device may assign to the button or set of buttons. Each button size, layout, location, and function may vary for each manufacturer and model of the medical diagnostic device 10.

A lancet port 20 is located at a bottom 22 of the medical diagnostic device 10. The lancet port 20 provides an opening through which the lancet structure can extend outwardly from the protective enclosure 14. The lancet structure may extend outwardly from the lancet port 20 to make an incision at a skin site of the patient and produce an amount of bodily fluid from the skin site of the patient. In one embodiment, the medical diagnostic device 10 is an in vitro diagnostic device that is used to test blood and other body fluids and tissues to obtain information for the diagnosis, prevention and treatment of a disease. The medical diagnostic device 10 may be a self-testing blood glucose meter for people with diabetes. In one embodiment, the medical diagnostic device 10 is a handheld reagent-based blood glucose meter, which measures glucose concentration by observing some aspect of a chemical reaction between a reagent and the glucose in a fluid sample. The reagent may be a chemical compound that is known to react with glucose in a predictable manner, enabling the monitor to determine the concentration of glucose in the sample. For example, the medical diagnostic device 10 may be configured to measure a voltage or a current generated by the reaction between the glucose and the reagent in one embodiment, electrical resistance in another embodiment, as well as a color change of the reagent in still another embodiment.

In some embodiments, the medical diagnostic device 10 is a mechanically-driven device where the protective enclosure 14 includes a winding assembly (not shown) that is operated using telescoping housing portions 25 and 27. FIG. 1 illustrates the telescoping housing portions 25 and 27 in their initial, uncocked positions. As will be described in greater detail below, the housing portions 25 and 27 may be moved relative to each other manually to place a lancet actuator assembly (not shown) in a wound, triggerable configuration. The lancet actuator assembly may be used to drive a lancet structure through the lancet port 20 to make an incision at a skin site of the patient and produce an amount of bodily fluid that can then be carried from the skin site of the patient. In some embodiments, the housing portion 27 includes a cartridge housing 29 with a removable door 31 for holding a lancet housing assembly (not shown) that includes multiple lancet structures. In other embodiments, the door 31 may be hinged to the housing portion 27, such that it can be rotated relative to the housing portion 27 to permit access to the cartridge housing 29 for removing or loading the lancet housing assembly. An indicator device 33 may be provided that provides the patient with information regarding the number of unused lancet structures available in the lancet housing assembly. In this embodiment, the indicator device 33 includes a window 35 in the removable door 31 that allows viewing of numbers provided on the lancet housing assembly as the lancet housing assembly is indexed within the cartridge housing 29.

Figure 2:
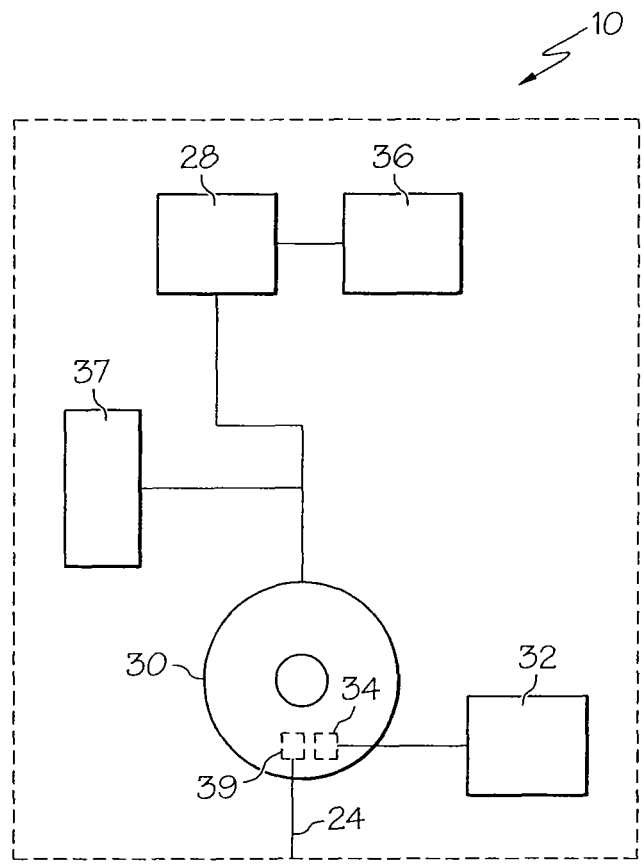
FIG. 2 is a schematic representation of the portable handheld medical diagnostic device of FIG. 1.
Figure 3:
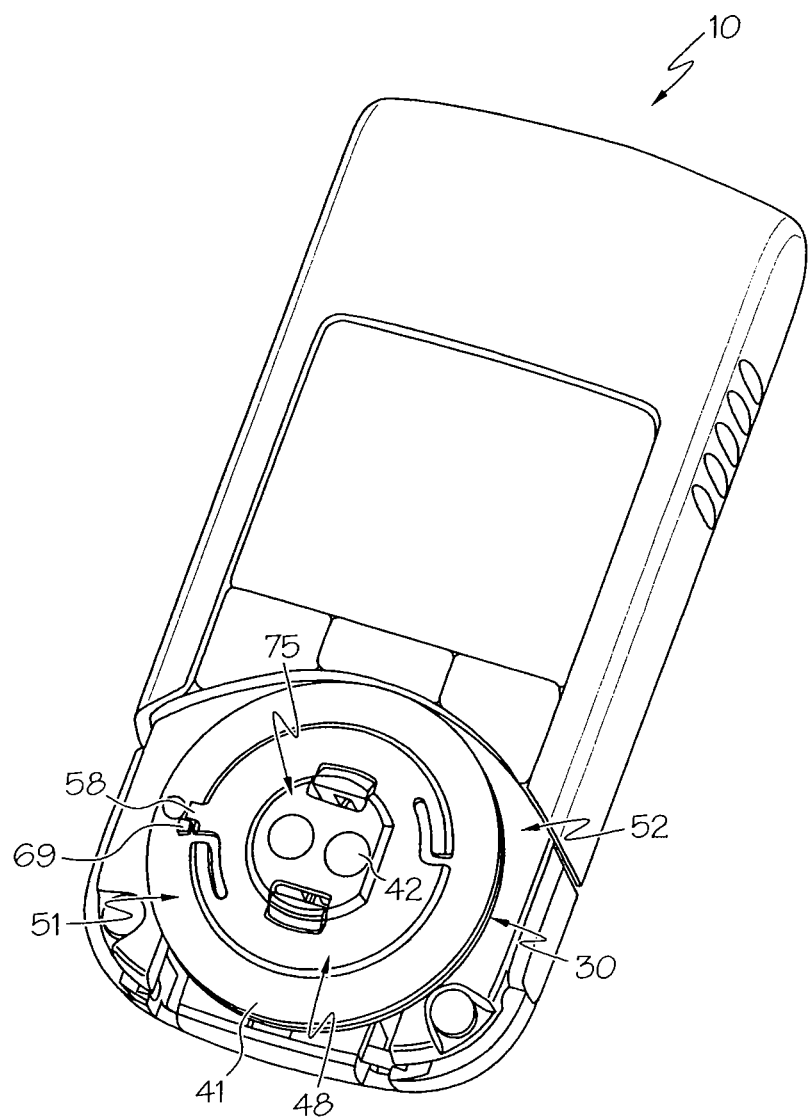
FIG. 3 is another perspective view of the portable handheld medical diagnostic device of FIG. 1 with an embodiment of a lancet housing assembly exposed.
Figure 4:
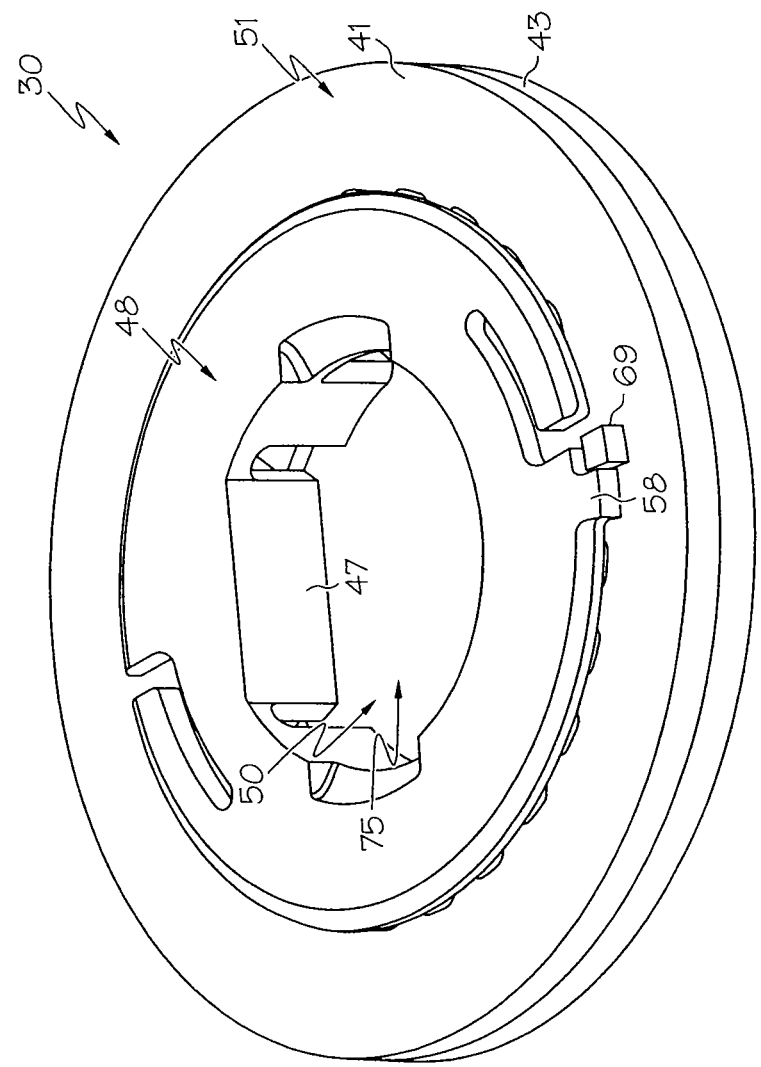
FIG. 4 is a perspective view of the lancet housing assembly of FIG. 3 in isolation.

Referring to FIG. 2, a simplified, schematic view of the medical diagnostic device 10 includes a number of features that allow for improved comfort and ease of use for a patient. In general, the medical diagnostic device 10 may include a lancet housing assembly 30 in the form of a cartridge or disk that is used to house multiple lancet structures 24 for use in the medical diagnostic device 10, a lancet actuator assembly 28 for extending and/or retracting the lancet structures 24 and a speed control mechanism 36 that engages the lancet actuator assembly 28 for adjusting the speed at which the lancet structure 24 is extended and/or retracted by the lancet actuator assembly 28. A depth adjustment mechanism 37 may also be provided that allows for adjustment of a penetration depth of the lancet structure 24 before extending the lancet structure 24.

A measurement system 32 may be provided that measures glucose concentration in a blood sample delivered to a test material 39, for example, using an optical device 34 in one embodiment for detecting a color change in a reagent or other suitable device in other embodiments, such as electrical contacts if measuring a change in an electrical characteristic/property of the reagent. The test material 39 may be employed to hold the reagent and to host the reaction between the glucose and the reagent mentioned above. In one embodiment, the test material 39 and the optical device 34 may be located such that the reaction between the glucose and the reagent may be read electronically in order for the measurement system 32 to determine the concentration of glucose in the sample and display the results to a user using the display device 12. These embodiments enable both health care professionals and patients to perform reliable decentralized testing in hospitals, clinics, offices or patients' homes.

Referring to FIGS. 3-6, in some embodiments, multiple lancet structures are housed in the lancet housing assembly in the form of a disk 30 that includes multiple lancet compartments 40 (FIG. 5) arranged in a radial fashion about a central axis 42. The disk 30 may have an outer protective housing (not shown) formed of any one or more suitable materials, such as plastics, foils, metals, and the like. Materials with sterile moisture barriers may be used to provide lancet compartments 40 with protected environments. In some embodiments, such as the one illustrated, the disk 30 may be formed by a center hub 48 and a disk component 51 that is configured to rotate relative to the center hub 48. In some embodiments, the disk component 51 includes an upper disk member 41 and a lower disk member 43 that is connected to the upper disk member 41. Any suitable connection may be used between the upper and lower disk members 41 and 43, such as laser welding, snap fit, press fit, adhesives, fasteners, and the likes.

Figure 5:
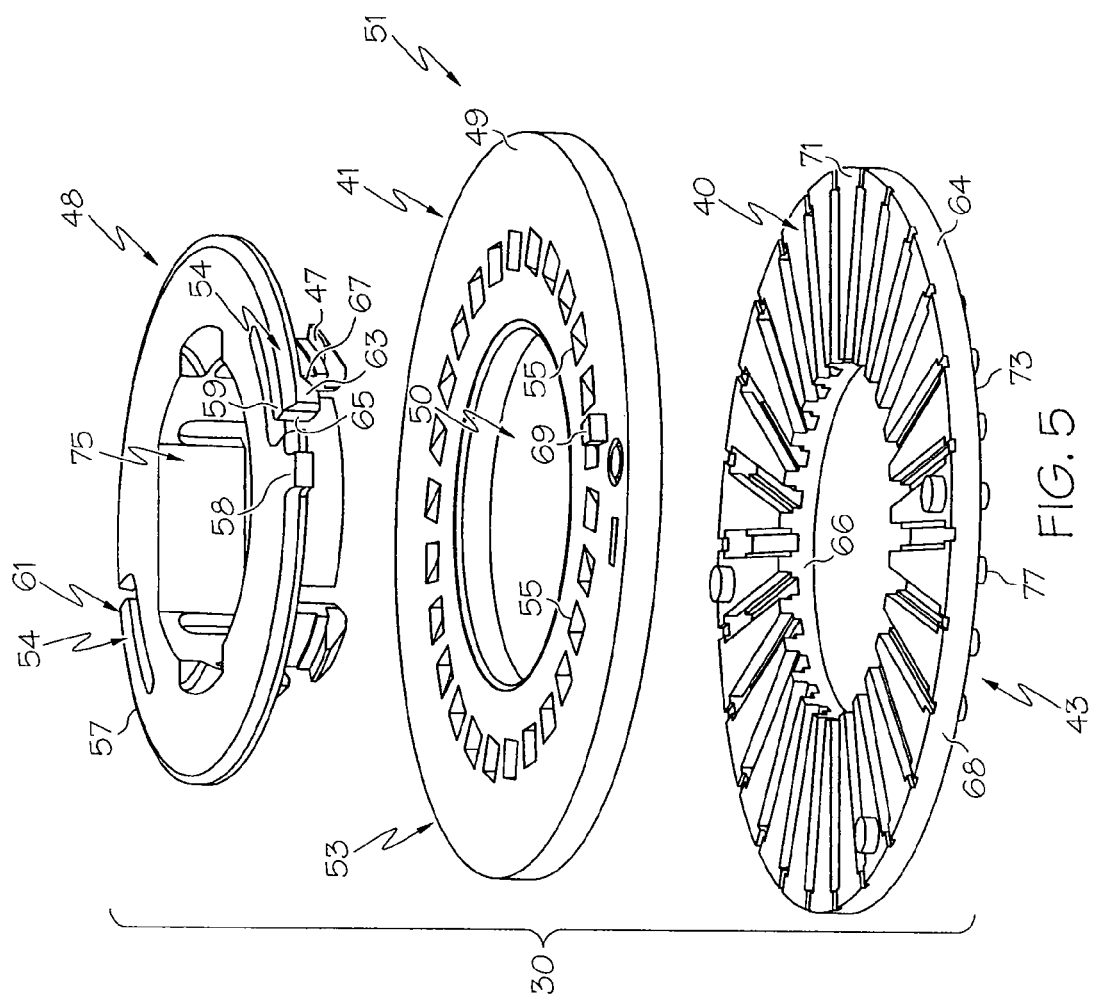
FIG. 5 is an exploded perspective view of the lancet housing assembly of FIG. 3.

As depicted in the exploded view of FIG. 5, the center hub 48 may be provided within a central bore 50 of the disk 30 such that it may rotate relative to the disk component 51. In one embodiment, the center hub 48 may be provided such that it may snap fit into place within the central bore 50 of the disk 30. For example, the center hub 48 may include fastening structures 47 in the form of hook-like projections that engage a bottom surface 73 of the disk component 51. Although the center hub 48 may be mounted rotatably within the central bore 50 of the disk 30 such that it may be removably retained therein, such as via the snap fit arrangement depicted in FIG. 5, or via a fastener(s) in another embodiment which provides a nut or clip (not shown) which engages a threaded or shaped end (not shown) of the center hub 48 adjacent the bottom surface 73, in other embodiments the center hub 48 may be provided rotatably therein but also retained permanently therein, such as via laser welding in another embodiment which provides a deformed free end (not shown) of the center hub 48 that flairs outwardly about the bottom surface 73. The center hub 48 may have a non-circular or irregular-shaped (e.g., D-shaped) key or opening 75 that allows for automatic alignment of the disk 30 in only one or more orientations for insertion into a disk compartment 52 of the medical diagnostic device 10. For example, in the illustrated embodiment, the D-shaped key may allow for automatic alignment of the disk 30 in only one orientation for insertion into the disk compartment 52.

Figure 6:
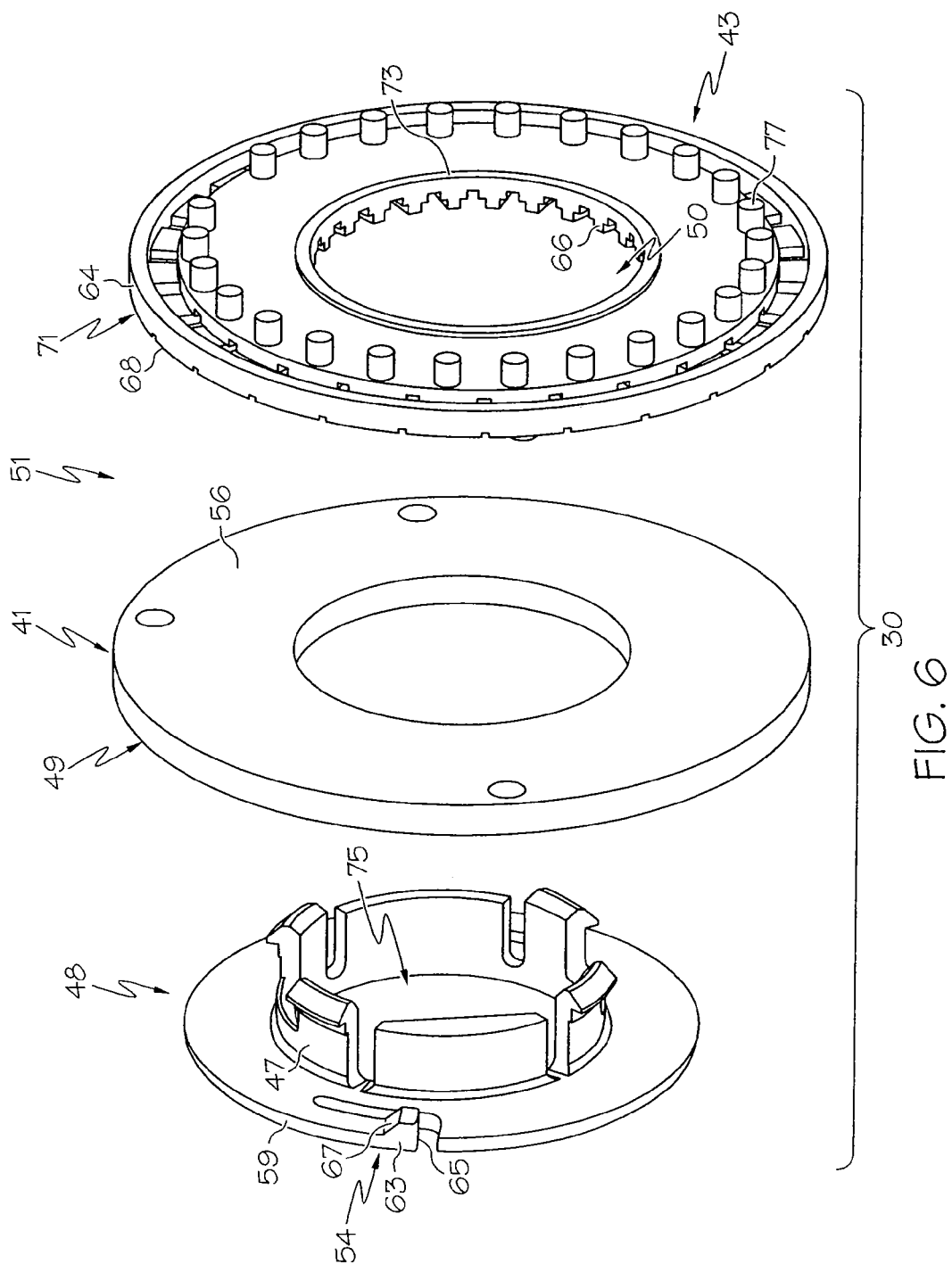
FIG. 6 is another exploded perspective view of the lancet housing assembly of FIG. 3.

In addition to FIG. 5, FIG. 6 also illustrates an exploded view of the disk 30 including the upper disk member 41 and the lower disk member 43 of the disk component 51 and the center hub 48. The upper disk member 41 includes a top surface 49 and a bottom surface 56 opposite the top surface 49. Numbered indicia 53 (FIG. 5) may be printed, molded, etched, machined, etc. onto the top surface 49 for providing the user an indication of the number of unused lancet structures 24 are remaining or have been used. The numbered indicia 53 may be viewed through the window 35 of the removable door 31 (FIG. 1). Notches 55 extend inwardly from the top surface 49 of the upper disk member 41. The notches 55 are spaced angularly from adjacent notches 55 and are located substantially equidistant from the center of the upper disk member 41. The notches 55 may each be associated with a respective lancet compartment 40 and provide engagement structure for preventing over rotation of the disk 30 relative to the center hub 48.

The center hub 48 may include rotation limiting structure 54 that cooperates with rotation limiting structure (e.g., the notches 55) of the upper disk member 41. The center hub 48 may include arm members 57 and 59, each having a downward protruding projection 61 and 63 that is sized and arranged to be removably received by the notches 55 as the upper disk member 41 rotates relative to the center hub 48. The projections 61 and 63 may each include a relatively vertically oriented side 65 and a relatively angled side 67 that is at an angle to the vertical. The vertically oriented side 65 can inhibit rotation of the upper disk member 41 relative to the center hub 48 while the angled side 67 allows rotation of the upper disk member 41 relative to the center hub 48 in the opposite direction. The arm members 57 and 59 may be formed of a somewhat flexible material to allow the arm members 57 and 59 to resiliently bend so that the projections 61 and 63 may move out of one notch 55 and be received by an adjacent notch 55 for locking the upper disk member 41 in an angular relationship relative to the center hub 48. Cooperating end stops 58 and 69 may also be provided to prevent rotation of the upper disk member 41 relative to the center hub 48 once the end stops 58 and 69 engage.

The lower disk member 43 includes a top surface 79, a bottom surface 73 opposite the top surface 79, an outer facing side 64 and an inner facing side 66. The lancet compartments 40 extend in a generally radial direction from the inner facing side 66 to the outer facing side 64. The lancet compartments 40 may be equally spaced an angular distance apart from one another and about the periphery of the lower disk member 43. As will be described in greater detail below, each lancet compartment 40 may include a lancet structure 24 that can extend through an opening 68 in each lancet compartment 40 and through the lancet port 20 of the medical diagnostic device 10. Extending downwardly from the bottom surface 73 of the lower disk member 43 are indexing pins 77. The indexing pins 77 may be used to rotate the disk component 51 relative to the center hub 48, for example, after each operation of the lancet structures 24.

Figure 7:
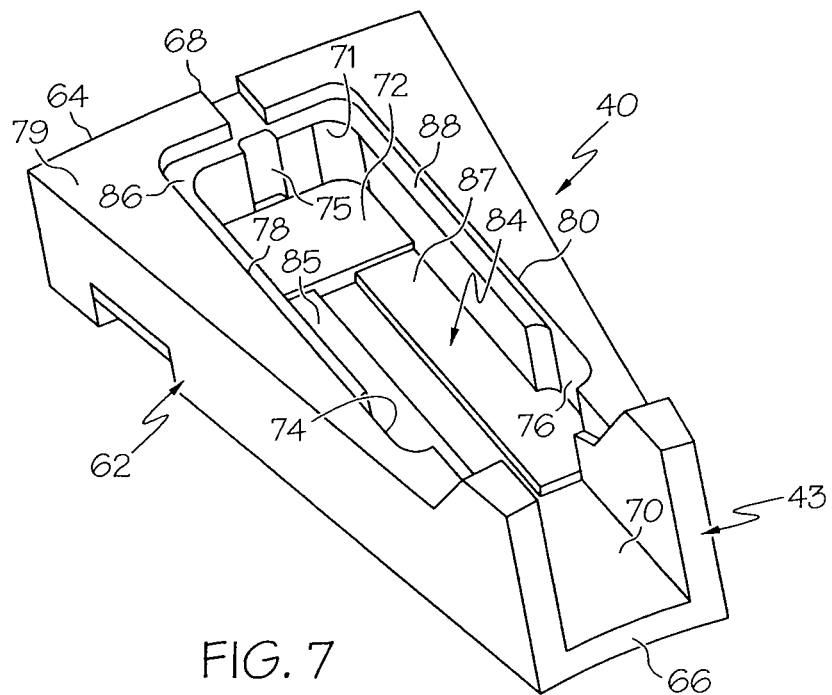
FIG. 7 is an embodiment of a lancet compartment for use with the lancet housing assembly of FIG. 3 without a lancet structure.
Figure 8:
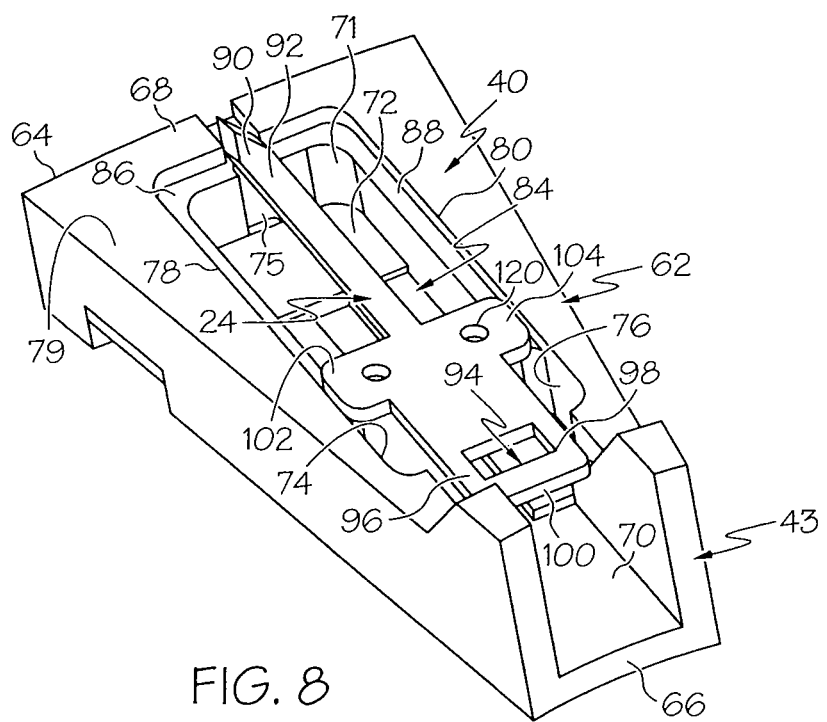
FIG. 8 illustrates the lancet compartment of FIG. 7 with an embodiment of a lancet structure.

Referring to FIGS. 7 and 8, an exemplary empty lancet compartment 40 and a lancet compartment 40 with an unused lancet structure 24 are shown, respectively. Referring first to FIG. 7, the lancet compartment 40 is formed, in part, by a compartment section 62 of the lower disk member 43. The upper disk member 41 is removed in FIGS. 7 and 8 for clarity. The compartment section 62 includes the outer facing side 64 and the inner facing side 66. The opening 68 is located at the outer facing side 64 that can align with the lancet port 20 located at the bottom 22 of the medical diagnostic device 10 (FIG. 1). Sidewalls 78 and 80 extend between the outer facing side 64 and the inner facing side 66. A clearance floor 70 extends from an inner wall 71 at the outer facing side 64 within the lancet compartment 40 to the inner facing side 66 and forms a lowermost floor of the lancet compartment 40. Adjacent the inner wall 71 of the lancet compartment 40 is a reagent material 72, which is located on the clearance floor 70 and within the lancet compartment 40. The reagent material 72 may be a test strip such as electrochemical type test strips, colorimetric or optical type test strips, etc. to name a few.

Drop down slots 74 and 76 are located in sidewalls 78 and 80 and extend vertically from the top surface 79 of the compartment section 62 to a lancet floor 84. Another drop down slot 75 is located in the inner wall 71 and extends vertically from the opening 68 to the reagent material 72. The lancet floor 84 extends along the clearance floor 70, in a raised relationship thereto, from the reagent material 72 back toward the inner facing side 66 and within the drop down slots 74 and 76. In some embodiments, the lancet floor 84 may be formed by a pair of strips 85 and 87 that extend along their respective sidewall 78 and 80 and spaced-apart from each other thereby exposing part of the clearance floor 70 therebetween. In some embodiments, the lancet floor 84 and the clearance floor 70 may both be part of the same floor structure. The lancet floor 84 provides clearance between the clearance floor 70 and the lancet structure 24 when the lancet structure is dropped down against the reagent material 72 and seated against the lancet floor 84. Lancet guide rails 86 and 88 extend along the sidewalls 78 and 80 and recessed vertically below the top surface 79 of the compartment section 62. In some embodiments, the lancet guide rails 86 and 88 extend substantially parallel to the lancet floor 84 and/or clearance floor 70 from the drop down slots 74 and 76 to the opening 68 with the drop down slot 75 intersecting the lancet guide rails 86 and 88 at the inner wall 71 and the drop down slots 74 and 76 intersecting the guide rails 86 and 88, respectively, at the sidewalls 78 and 80.

Referring to FIG. 8, the lancet compartment 40 is illustrated with a lancet structure 24. The lancet structure 24, in this exemplary embodiment, includes a skin penetrating end 90 and a blood transport portion 92 adjacent the skin penetrating end 90. In some embodiments, the blood transport portion 92 may include one or more capillary structures that facilitate movement of the bodily fluid away from the skin penetrating end to the blood transport portion 92. The skin penetrating end 90, when extended through the opening 68, is shaped and sized to penetrate the patient's skin at a skin location in order to provide an amount of blood. The blood transport portion 92 can receive the amount of blood from the skin penetrating end 90 and be used to carry the amount of blood away from the skin location.

A drive member connecting structure 94 is located at an end 96 that is opposite the skin penetrating end 90. In this embodiment, the drive member connecting structure 94 is a closed opening 98 having a rear ledge 100 that is used to engage the drive member 95 (e.g., in the form of a drive hook). Rail riding structure in the form of outwardly extending wings 102 and 104 are located between the drive connecting structure 94 and the blood transport portion 92. The wings 102 and 104 extend outwardly in the widthwise direction to ride along the lancet guide rails 86 and 88 when extending and retracting the lancet structure 24.

Figure 9:
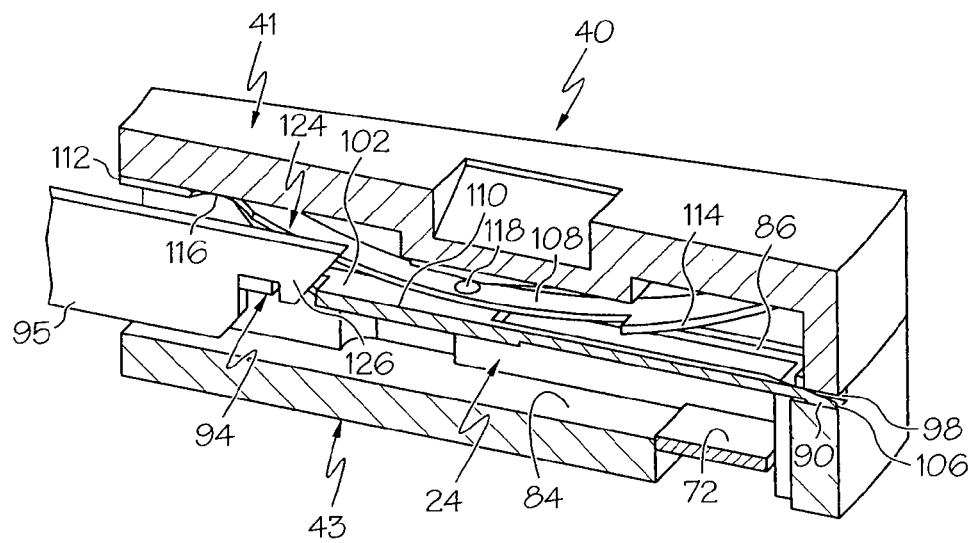
FIG. 9 illustrates the lancet compartment of FIG. 7 with the lancet structure in operation.

Referring to FIG. 9, a cross-section of the lancet compartment 40 is illustrated in an assembled configuration with the upper disk member 41 connected to the lower disk member 43 thereby providing the lancet compartment 40 therebetween. The drive member 95 extends into the lancet compartment 40 and is illustrated releasably engaged with the drive member connecting structure 94 of the lancet structure 24. The skin penetrating end 90 of the lancet structure 24 is illustrated as resting on a bottom surface 106 of the opening 68 while the wings (only wing 102 is partially shown) rest on the lancet guide rails (only guide rail 86 is partially shown).

A biasing mechanism 108 (e.g., a flat spring) extends into the lancet compartment 40, toward the lancet floor 84 and engages a surface 110 of the lancet structure 24. The biasing mechanism 108 may be connected at opposite ends 112 and 114 to a ceiling 116 of the upper disk member 41. A projection 118 formed in the biasing mechanism 108 may be provided that mates with a corresponding detent 120 of the lancet structure 24 (FIG. 8). In another embodiment, the lancet structure 24 may include the projection 118 and the biasing mechanism 108 may include the detent 120. Any other suitable mating arrangement can be used, such as opposing ramp structures. This mating arrangement can provide added resistance to unintended movement of the of the skin penetrating end 90 of the lancet structure 24 through the opening 68.

Figure 10:
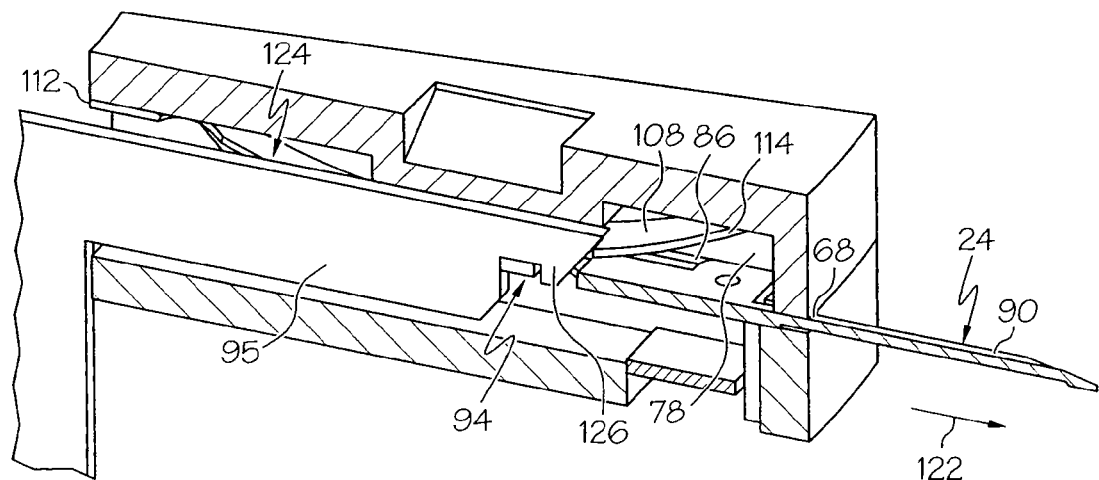
FIG. 10 illustrates the lancet compartment of FIG. 7 with the lancet structure in operation.

Referring to FIG. 10, the lancet structure 24 may be extended through the opening 68 in the direction of arrow 122 using the drive member 95 that is connected to the drive member connecting structure 94. As can be seen by FIGS. 9 and 10, the biasing mechanism 108 may include a slot 124 that is formed along a length of the biasing mechanism 108, between the ends 112 and 114. The slot 124 may be sized to receive a hook portion 126 of the drive member 95 and to allow movement of the drive member 95 through the slot 124 and toward the opening 68. In some embodiments, the hook portion 126 of the drive member 95 is received within the slot 124 such that the biasing mechanism 108 maintains contact with the lancet structure 24 as the lancet structure 24 is being driven toward the opening 68. As the lancet structure 24 is driven toward the opening 68, the outwardly extending wings 102 and 104 ride along the lancet guide rails 86 and 88 of the sidewalls 78 and 80.

Figure 11:
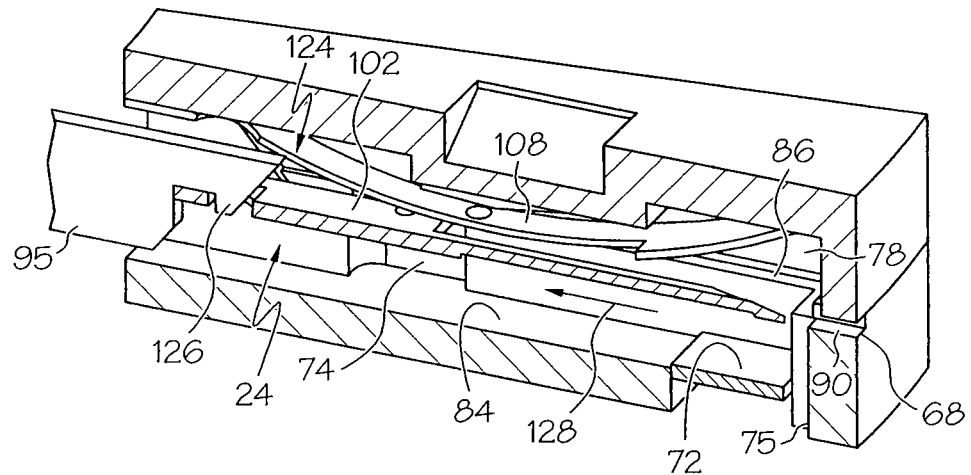
FIG. 11 illustrates the lancet compartment of FIG. 7 with the lancet structure in operation.

Referring to FIG. 11, the lancet structure 24 may be retracted from the opening 68 in the direction of arrow 128 using the drive member 95. The hook portion 126 of the drive member 95 may be received within the slot 124 such that the biasing mechanism 108 maintains contact with the lancet structure 24 as the lancet structure 24 is being driven away from the opening 68. As shown in FIG. 11, once the outwardly extending wings 102 and 104 that ride along the lancet guide rails 86 and 88 of the sidewalls 78 and 80 align with the drop down slots 74 and 76, and the skin penetrating end 90 aligns with or moves beyond the drop down slot 75, the biasing mechanism 108 forces the lancet structure 24 in a direction substantially transverse to the retract direction 128, toward the lancet floor 84 and the reagent material 72. Thus, the biasing mechanism 108 can be used to automatically deliver the lancet structure 24 to the reagent material 72 as the lancet structure 24 is retracted by the drive member 95.

Figure 12:
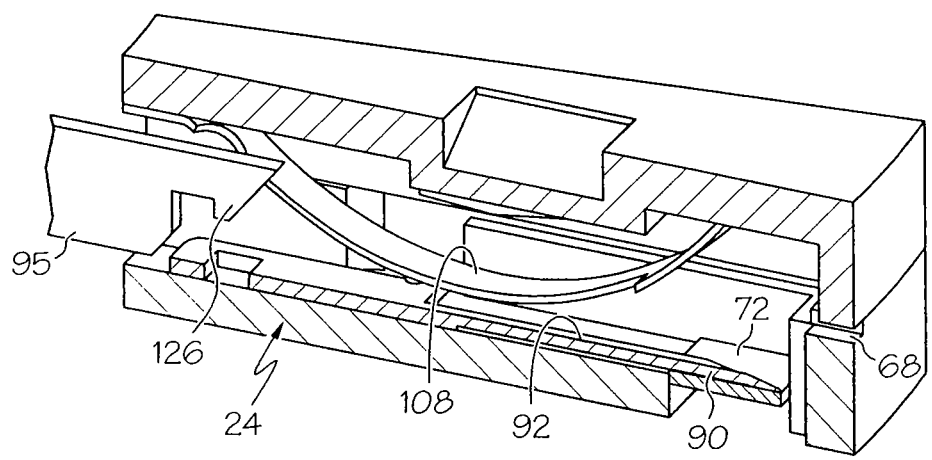
FIG. 12 illustrates the lancet compartment of FIG. 7 with the lancet structure in operation.

Referring to FIG. 12, the lancet structure 24 is illustrated fully retracted and directed toward the reagent material 72. In this position, the skin penetrating end 90 and the blood transport portion 92 of the lancet structure 24 are offset from the opening 68 (i.e., out of alignment with the opening 68) and in contact with the reagent material 72 such that blood can be transferred to the reagent material 72. In addition to delivering the lancet structure 24 to the reagent material 72, the offset arrangement of the skin penetrating end 90 out-of-alignment with the opening 68 can also inhibit unintended extension of the skin penetrating end 90 through the opening 68 by the drive member 95, which no longer can engage and extend the lancet structure 24. In particular, in the illustrated embodiment should the drive member 95 once again move towards the opening 68 of the lancet compartment 40 containing a used lancet structure 24, the drive member 95 will pass over the lancet structure 24 due to the offset arrangement also placing the drive member connecting structure 94 of the lancet structure 24 out-of-alignment with drive member 95. Accordingly, the biasing mechanism 108 providing the lancet structure 24 in the offset arrangement after the transfer of blood from the blood transport portion 92 of the lancet structure 24 to the reagent material 72, provides a convenient fail safe.

Figure 13:
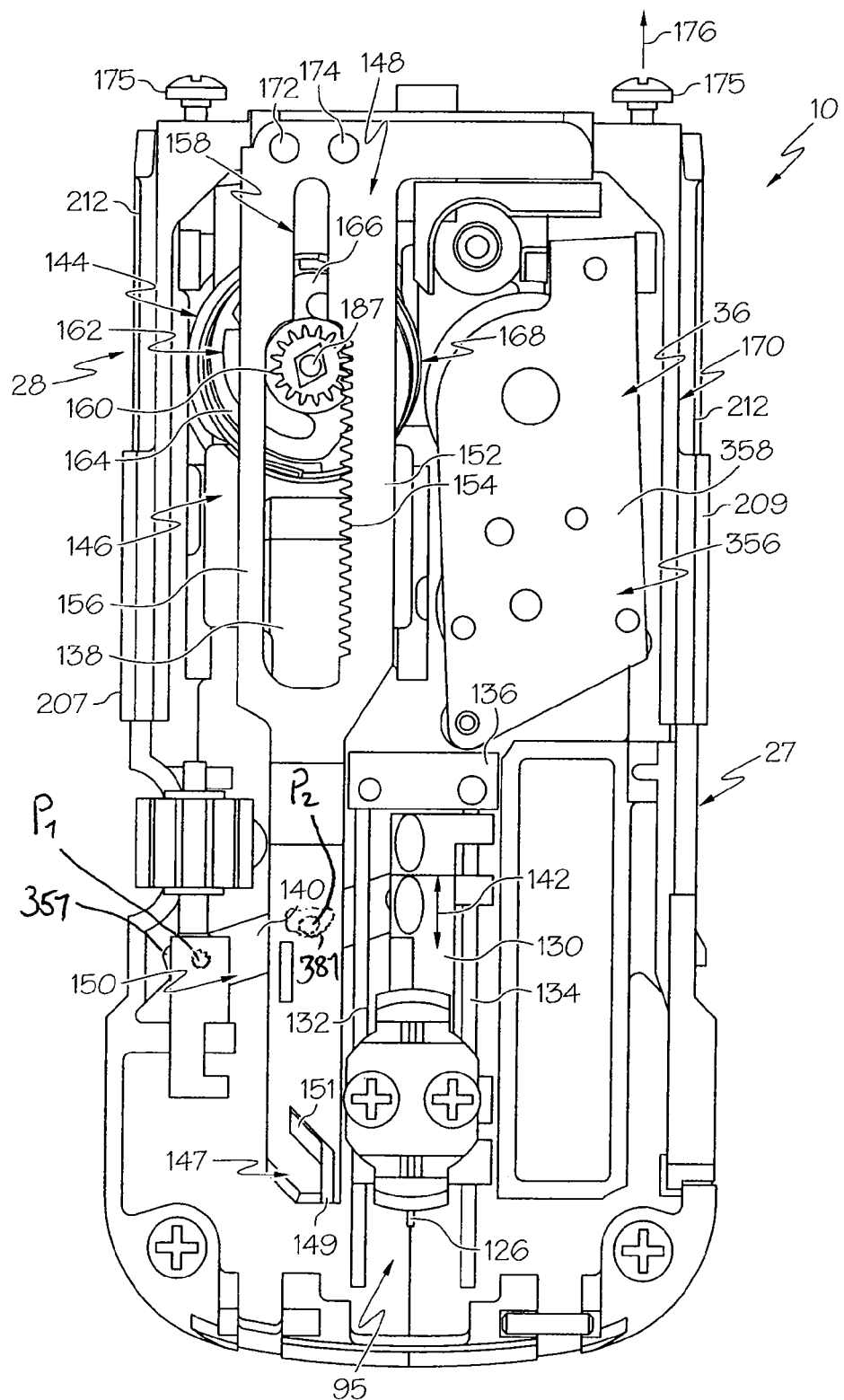
FIG. 13 illustrates the portable handheld medical diagnostic device of FIG. 1 with a portion of the housing removed.

Referring to FIG. 13, the drive member 95 including the hook portion 126 is operatively connected to the lancet actuator assembly 28, which is used to extend and retract the drive member 95. The drive member 95 is connected to a hook arm 130. The hook arm 130 can slide along a pair of guide rails 132 and 134, which are used to accurately guide the drive member 95 toward extended and retracted positions. The guide rails 132 and 134 are fixedly connected to the housing portion 27 by an anchor 136. The hook arm 130 is connected to a follower arm 138 by an adjustable linkage 140. The follower arm 138 is driven in opposite directions (represented by arrows 142) by a clockwork spring drive assembly 144, which, in turn, moves the hook arm 130 and drive member 95 between their extended and retracted positions.

A rack member 146 is used to wind the clockwork spring drive assembly 144 and includes a rack portion 148 and a disk indexing portion 150. The rack portion 148 includes a first bar 152 having teeth 154 along its length and a second bar 156 having no teeth that is spaced from the first bar 152 by a slot 158. The teeth 154 are meshed with teeth 160 of a cam gear 162 having arms 164 and 166 that can engage a spring wheel assembly 168 (e.g., when rotating in only one direction, such as clockwise) for rotating the spring wheel assembly 168.

The rack member 146 may also include an indexing component 147 that is used to engage the indexing pins 77 of the disk 30. The indexing component 147 may include a pin engagement structure 149 including a ramp portion 151. As the rack member 146 is moved backward, the ramp portion 151 may engage one of the indexing pins 77, forcing the disk component 51 to rotate relative to the center hub 48.

The rack member 146 is connected to a slidable cam housing assembly 170 (e.g., using a pair of pins 172 and 174 or any other suitable connection). The slidable cam housing assembly 170 is connected to the telescoping housing portion 25 (e.g., using fasteners 175) such that movement of the telescoping housing portion 25 relative to the telescoping portion 27 moves the rack member 146 relative to the clockwork spring drive assembly 144. As can be appreciated from FIG. 13 and from the description below, movement of the rack member 146 in the direction of arrow 176 causes the cam gear 162 to rotate in the counterclockwise direction. Rotating counterclockwise, the cam gear 162 may not engage the spring wheel assembly 168 and may rotate relative thereto. Thus, moving the telescoping portion 27 outwardly in the direction of arrow 176 places the rack member 146 in a preload or pre-primed position that is ready to wind or prime the clockwork spring drive assembly 144 during its return stroke. Movement of the rack member 146 in a direction opposite arrow 176 causes the cam gear 162 to rotate in the clockwise direction. Rotating clockwise, the cam gear 162 engages the spring wheel assembly 168 thereby rotating the spring wheel assembly 168 in the clockwise direction, which can wind the clockwork spring drive assembly 144, as will be described in greater detail below.

Figure 14:
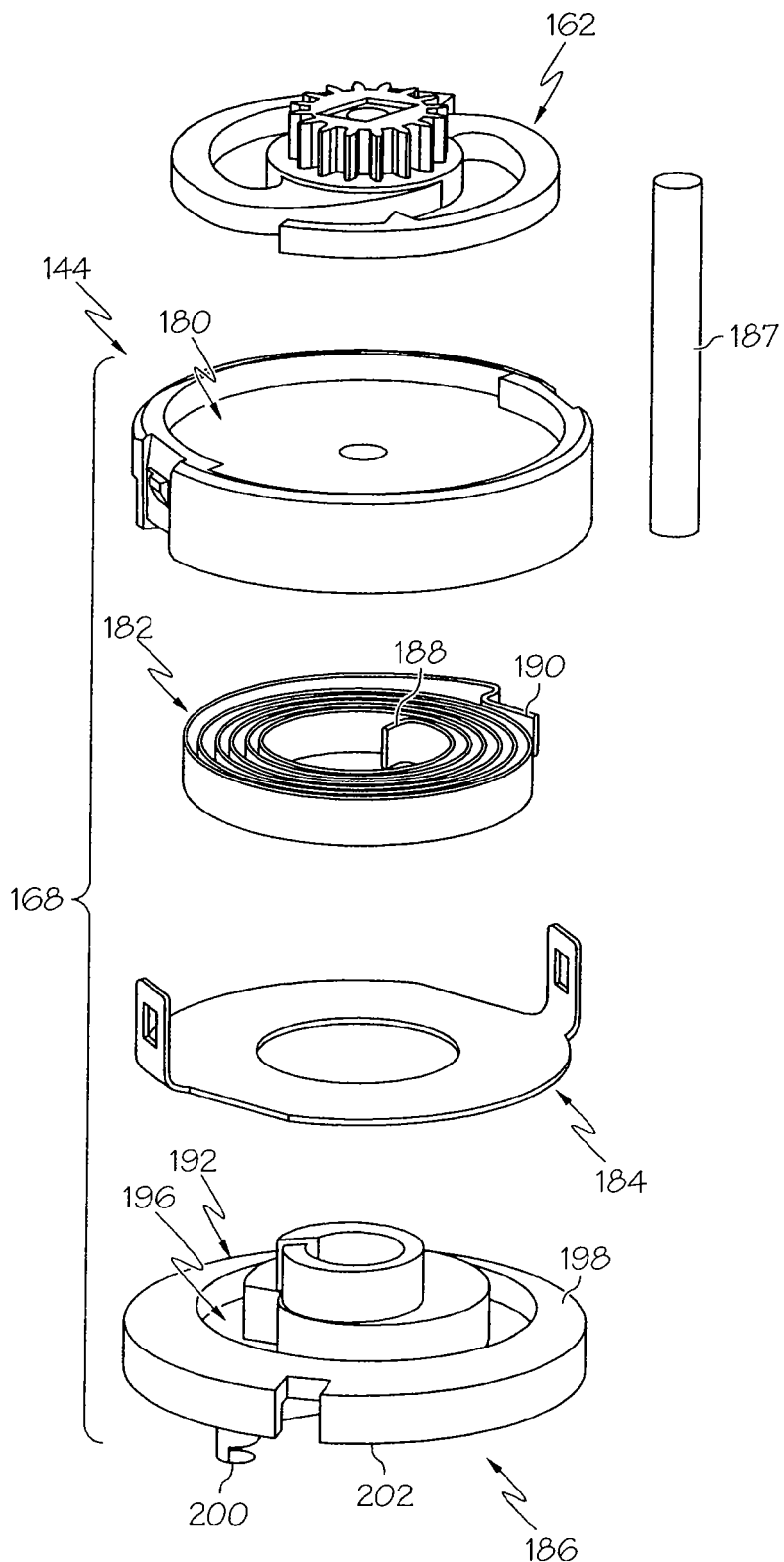
FIG. 14 is an exploded view of an embodiment of a spring-drive motor for use in the portable handheld medical diagnostic device of FIG. 1.

FIG. 14 illustrates an exploded view of the exemplary clockwork spring drive assembly 144 in isolation. The clockwork spring drive assembly 144 includes the cam gear 162 and the spring wheel assembly 168. The spring wheel assembly 168 includes a spring wheel 180, a torsion spring 182, a cover plate 184 and a roller wheel 186. The spring 182 connects the spring wheel 180 to the roller wheel 186 with the cover plate 184 providing a smooth, relatively low friction surface between the spring 182 and the roller wheel 186. At an inner end 188, the spring 182 is connected to the roller wheel 186, while at an outer end 190, the spring 182 is connected to the spring wheel 180. Rotation of the spring wheel 180 relative to the roller wheel 186 about a pivot axle 187 causes the spring 182 to wind thereby increasing the stored energy in the spring 182.

The roller wheel 186 includes a face cam portion 192 including a groove 196 that is provided at a face 198 of the roller wheel 186. The groove 196 provides a track that is followed by the follower arm 138 (FIG. 13) such that the follower arm 138 is moved a fixed distance between extended and retracted positions as the roller wheel 186 rotates. A follower pin 200 is provided at an opposite face 202 of the roller wheel 186. Rotation of the roller wheel 186 (and thus movement of the follower arm) is controlled through interaction between the follower pin 200 and a cam track portion of the slidable cam housing assembly 170.

Figure 15:
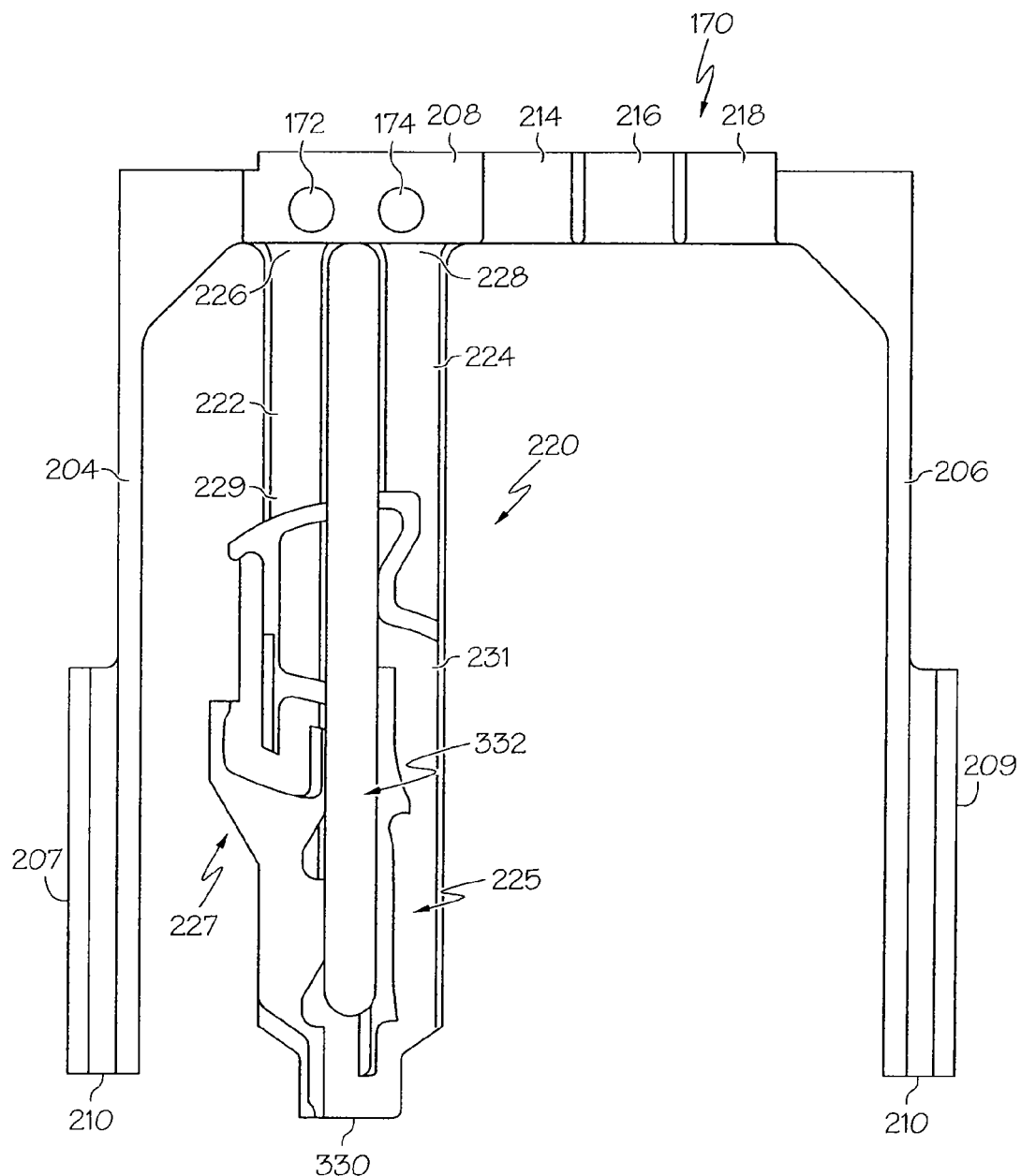
FIG. 15 is a top view of an embodiment of a slidable cam housing assembly for use with the spring-drive motor of FIG. 14.

Referring to FIG. 15, the slidable cam housing assembly 170 is depicted in isolation and includes a first side member 204, a second side member 206 and an end member 208 that extends between the first and second side members 204 and 206 thereby forming a somewhat U-shape. At each first and second side member 204 and 206 is a respective slidable rail 207, 209 that, in the illustrated embodiment, have a U-shaped groove 210 for slidably receiving a rail 212 of the housing portion 27 (FIG. 13) thereby forming a slide/rail assembly. The end member 208 includes the pins 172 and 174 for connecting the rack member 146 thereto and spring housing structures 214, 216 and 218, each for receiving a coil spring.

A track portion 220 extends outwardly from the end member 208 and generally between the first and second side members 204 and 206. The track portion 220 is formed by a pair of track support members 222 and 224 that are cantilevered at one end 226 and 228 to the end member 208 and extend outwardly to a joined free end 330. A slot 332 extends along a length of the track portion 220 that is sized to receive the pivot axle 187 of the clockwork spring drive assembly 144 such that the slidable cam housing assembly 170 can slide by the pivot axle 187. Carried by each of the track support members 222 and 224 is a respective elongated guide track element 225 and 227 that extends upwardly from top surfaces 229 and 231 of each track support member 222 and 224. The guide track elements 225 and 227 are used to control winding and releasing of the clockwork spring drive assembly 144 by controlling (i.e., allowing and disallowing) rotation of the roller wheel 186.

Figure 16:
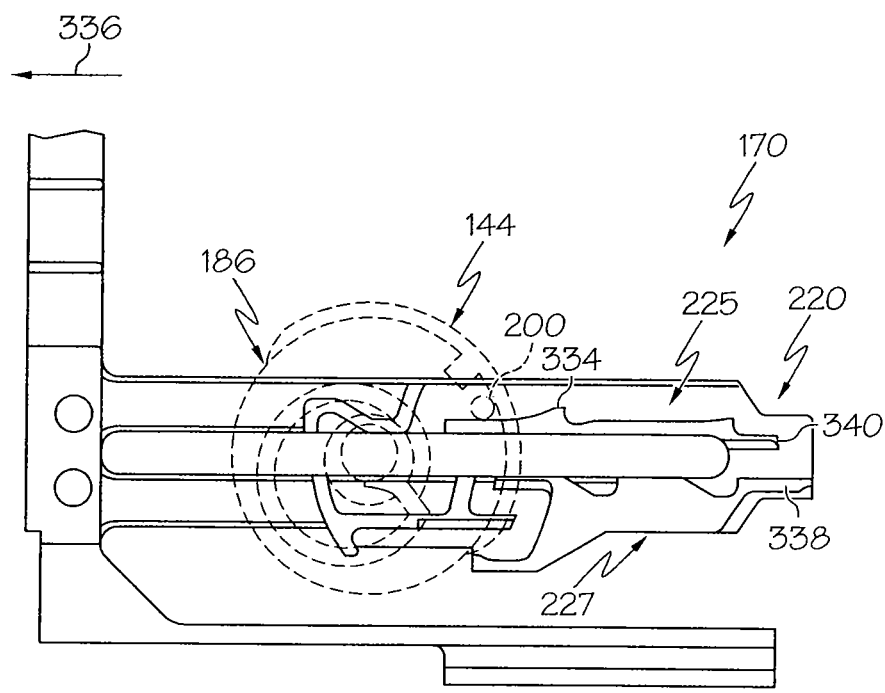
FIG. 16 illustrates the slidable cam housing assembly of FIG. 15 in operation with the spring-drive motor of FIG. 14.
Figure 17:
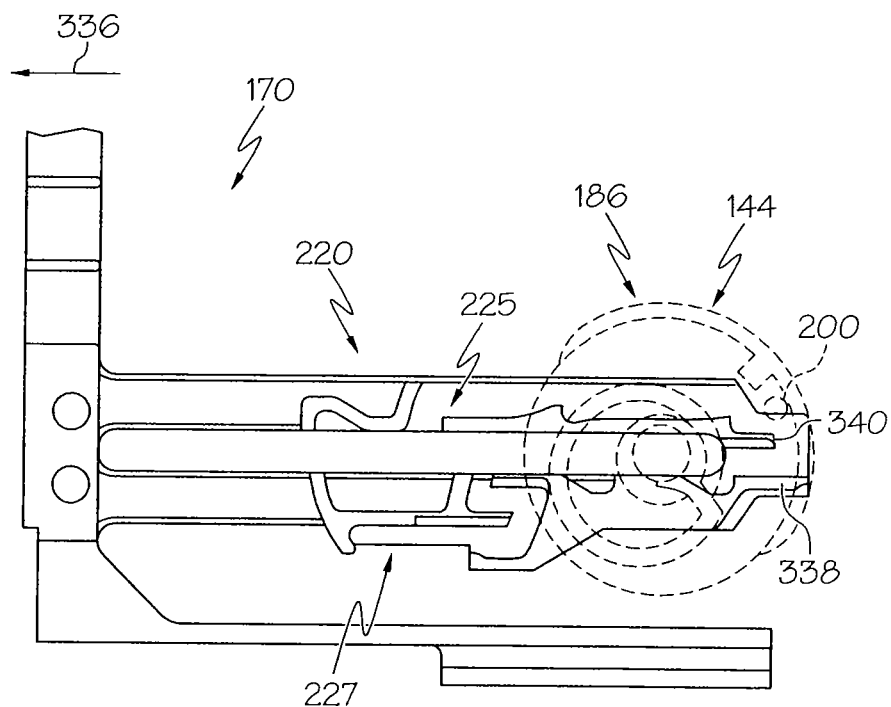
FIG. 17 illustrates the slidable cam housing assembly of FIG. 15 in operation with the spring-drive motor of FIG. 14.

FIGS. 16-20 illustrate a priming and firing sequence utilizing the clockwork spring drive assembly 144 and the slidable cam housing assembly 170. The roller wheel 186 is shown somewhat transparent such that the follower pin 200 can be seen as it interacts with the track portion 220 and the guide track elements 225 and 227. FIG. 16 illustrates the roller wheel 186 and the slidable cam housing assembly 170 in a start position with the follower pin 200 biased clockwise against a wall portion 334 of the guide track element 225 by the spring 182. In this position, the slidable cam housing assembly 170 can be pulled in the direction of arrow 336 relative to the clockwork spring drive assembly 144 through the connection of the slidable cam housing assembly 170 with the housing portion 25 and due to the clockwork spring drive assembly 144 being rotatably connected to the housing portion 27. FIG. 17 illustrates the slidable cam housing assembly 170 in a fully pre-primed position with the follower pin 200 biased against a wall portion 338 of the guide track element 227. As indicated above, movement of slidable cam housing assembly 170 and the rack member 146 connected thereto (FIG. 13) in the direction of arrow 336 causes the cam gear 162 to rotate in the counterclockwise direction. Rotating counterclockwise, the cam gear 162 may not engage the spring wheel assembly 168 and may rotate relative thereto without winding the spring 182. However, the spring 182 may be preloaded an amount such that the follower pin 200 moves against the guide track element 225, over an edge 340 of the guide track element 225 and to the wall portion 338 of the guide track element 227 in the fully pre-primed position.

Figure 18:
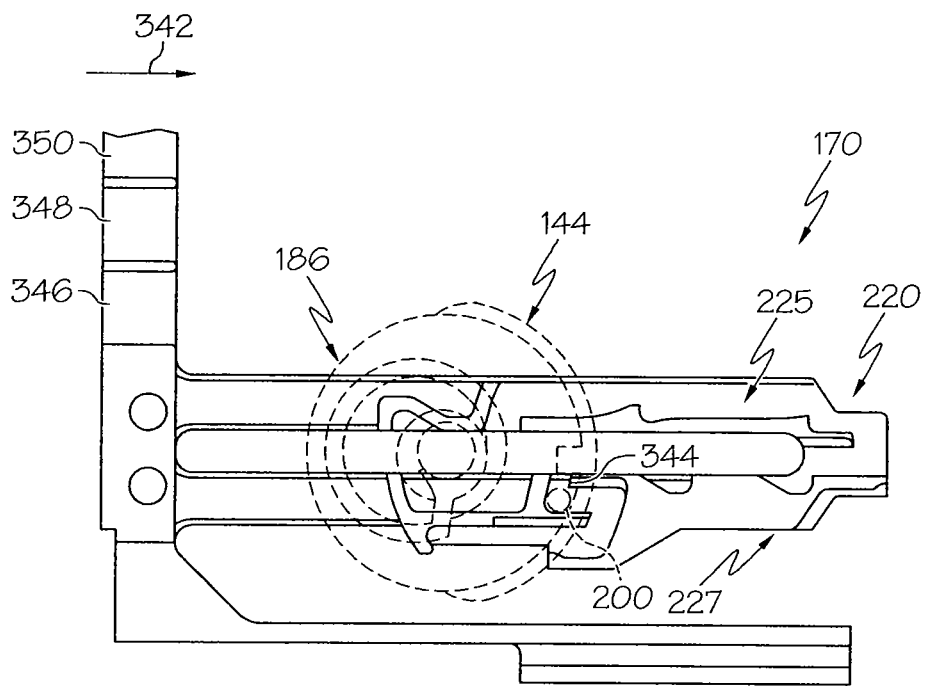
FIG. 18 illustrates the slidable cam housing assembly of FIG. 15 in operation with the spring-drive motor of FIG. 14.

Referring now to FIG. 18, the slidable cam housing assembly 170 may be pushed in the direction of arrow 342 toward a wound, triggerable position (or primed position) once placed in the fully pre-primed position with the follower pin between the guide track elements 225 and 227. As the slidable cam housing assembly 170 is pushed in the direction of arrow 342, the movement of slidable cam housing assembly 170 and the rack member 146 connected thereto (FIG. 13) in the direction of arrow 342 causes the cam gear 162 to rotate in the clockwise direction. Rotating clockwise, the cam gear 162 engages the spring wheel assembly 168 thereby rotating the spring wheel assembly 168 and winding the spring 182. The guide track element 227 prevents rotation of the roller wheel 186, which allows the spring 182 to wind relative to the roller wheel 186 as the spring wheel assembly 168 rotates.

The follower pin 200 follows along the guide track element 227 until the follower pin 200 reaches an opening 344. The follower pin 200 may then be rotated into the opening 344 due to the bias force provided on the roller wheel 186 by the spring 182. With the follower pin 200 in this position, the slidable cam housing assembly 170 is in a primed, safety-ready position. Biasing members 346, 348 and 350 (e.g., coil springs) may be provided that provide a slight spring back force once the slidable cam housing assembly 170 in the primed, safety-ready position shown by FIG. 18. The slight spring back force causes the slidable cam housing assembly 170 to move a relatively short distance in the pull direction of arrow 336, which allows the follower pin 200 to rotate around an edge 352 of the guide track element 227 and into the wound, triggerable position illustrated by FIG. 19.

Figure 19:
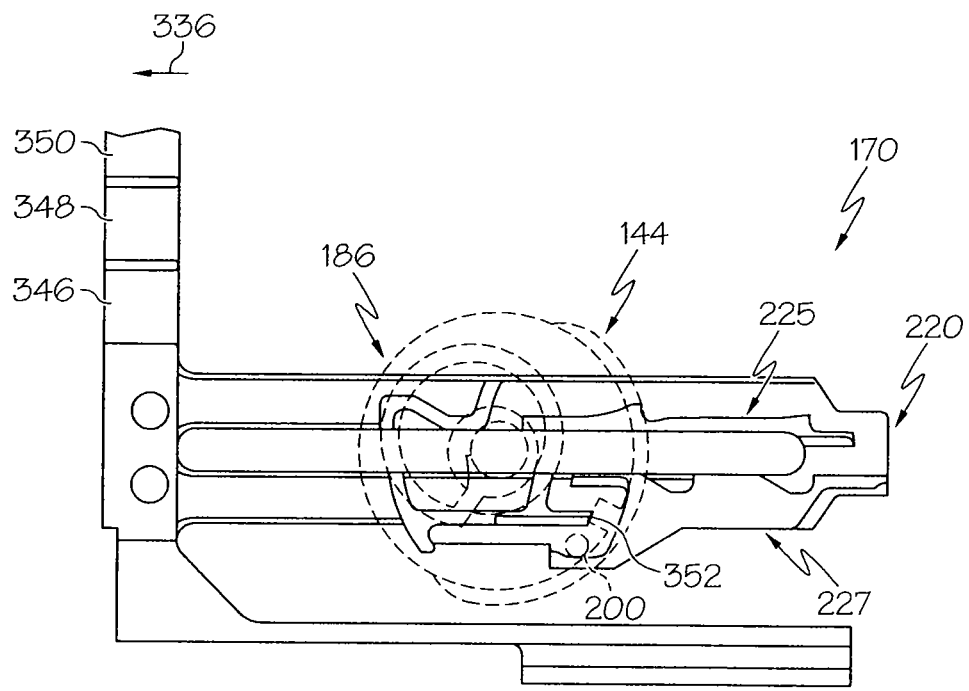
FIG. 19 illustrates the slidable cam housing assembly of FIG. 15 in operation with the spring-drive motor of FIG. 14.
Figure 20:
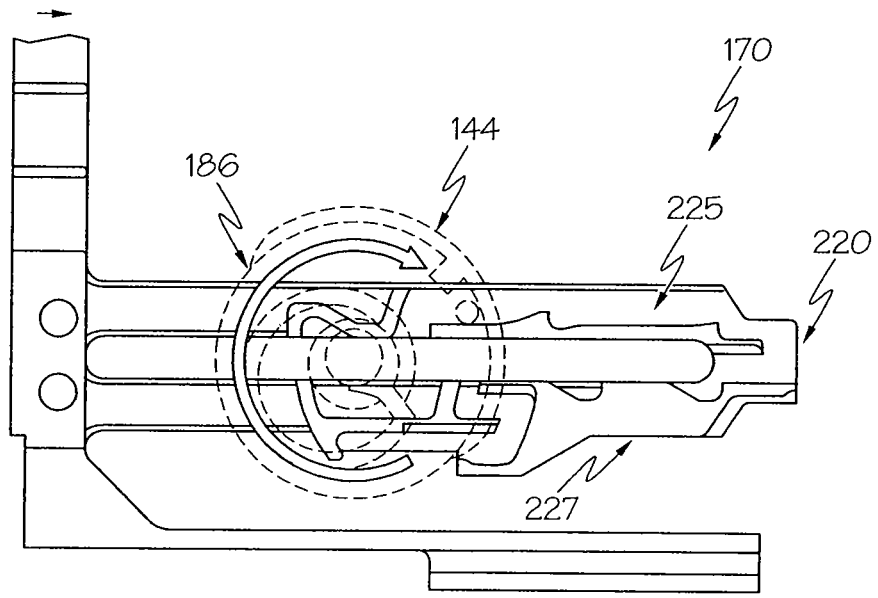
FIG. 20 illustrates the slidable cam housing assembly of FIG. 15 in operation with the spring-drive motor of FIG. 14.

Once the follower pin 200 is in the wound, triggerable position of FIG. 19, the medical diagnostic device 10 is ready to fire the lancet structure 24 through the lancet port 20. Triggering the medical diagnostic device 10 may be accomplished by placing the finger or other body part on the lancet port 20, pushing the housing portion 25 toward the housing portion 27 and overcoming the bias provided by the biasing members 346, 348 and 350. Referring to FIG. 20, the roller wheel 186 rotates due to the bias provided by the spring 182 once the follower pin 200 moves beyond a release point 354 provided by the guide track element 227. Rotation of the roller wheel 186 causes the lancet structure 24 to extend outwardly from the lancet port 20 and retract back into the lancet port 20.

In some embodiments, a velocity profile of the lancet structure 24 when being extended and retracted using the clockwork spring drive assembly 144 may be controlled such that the velocity profile is asymmetric during the extending and retracting phases. Such control can affect impact, retraction velocity and dwell time of the skin penetrating end 90 of the lancet structure 24.

Figure 21:
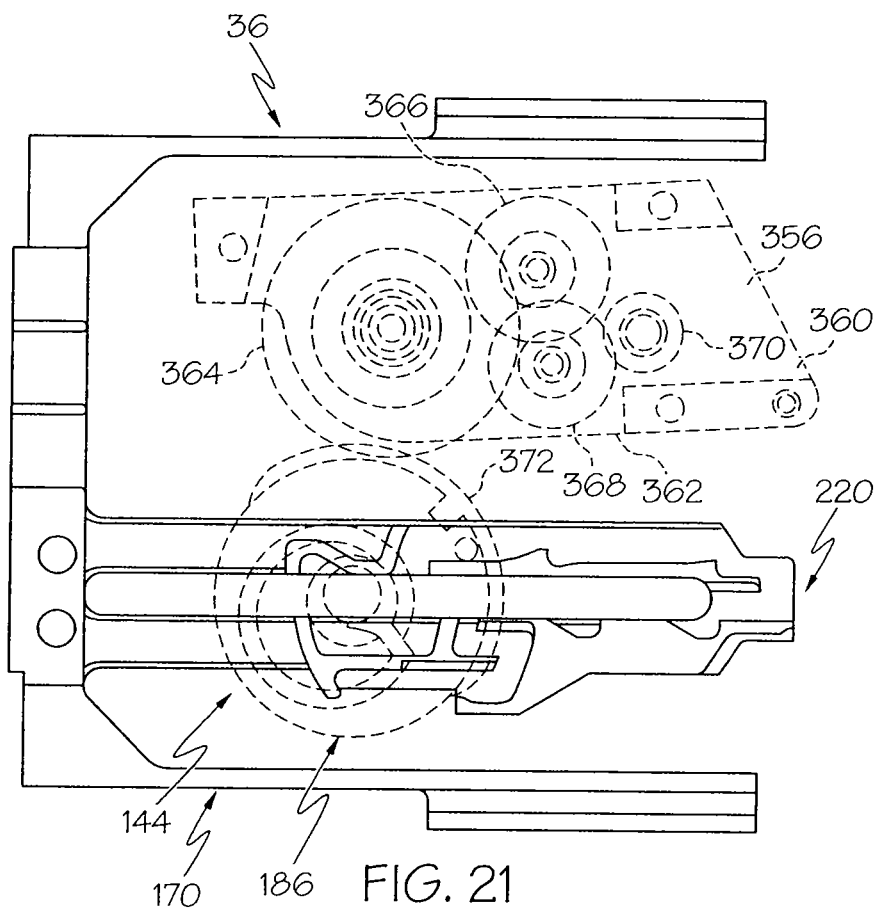
FIG. 21 illustrates the slidable cam housing assembly of FIG. 15 in operation with the spring-drive motor of FIG. 14 and an embodiment of a speed control mechanism.
Figure 22:
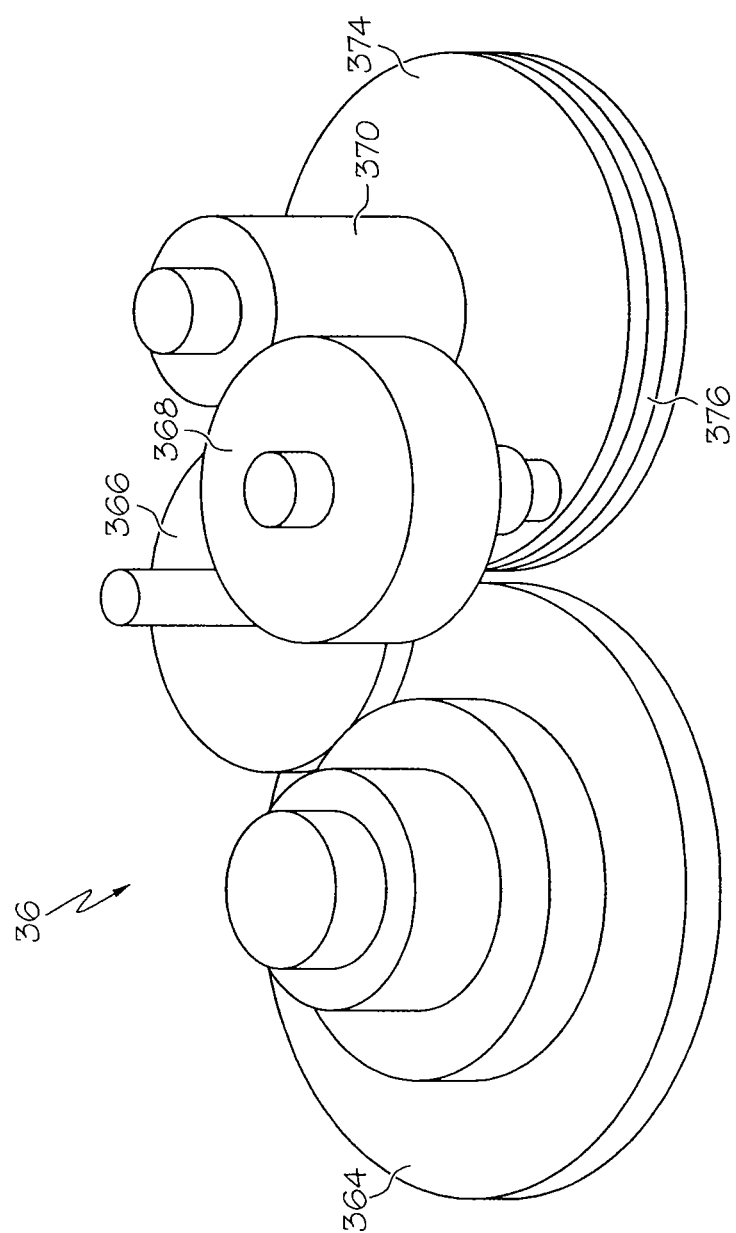
FIG. 22 illustrates components of the speed control mechanism of FIG. 21 in isolation.

Referring again to FIG. 13 and also to FIG. 21, the speed control mechanism 36 may be a gearbox and includes a housing 356 including a top wall 358, a bottom wall 360 and sidewalls 362. Located at least partially in the housing are gears 364, 366, 368 and 370. Referring also to FIG. 22, the gear 364 is an engagement gear and engages the clockwork spring drive assembly 144 as the roller wheel 186 rotates. In one embodiment, the roller wheel 186 includes an eccentric ring member 372 (e.g., formed of rubber or plastic) that increases the diameter of the roller wheel 186 at a particular location at the periphery of the roller wheel 186. As the roller wheel 186 rotates during the return stroke of the lancet structure 24, the eccentric ring member 372 engages the gear 364 thereby rotating the gear 364 and slowing the roller wheel 186. As the gear 364 rotates, it causes the gears 366, 368 and 370 to rotate. Gear 370 includes a flywheel 374 with weights 376 that are selected to mechanically slow the roller wheel 186 a selected amount. In some embodiments, the gear ratio provided by the gears 364, 366, 368 and 370 may be about 18:1 and the mass of the flywheel 374 may be less than one gram, such as about 0.67 gram.

Figure 23:
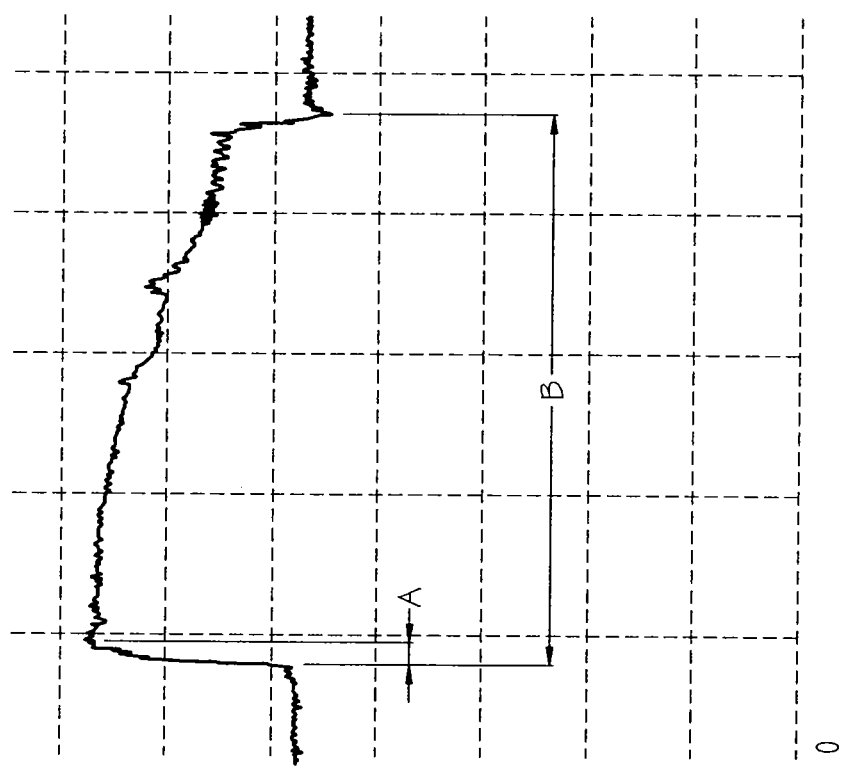
FIG. 23 illustrates an example of a velocity control profile using the speed control mechanism of FIG. 21.

Referring to FIG. 23, an exemplary velocity over time profile of the lancet structure 24 is illustrated. As can be seen, portion A shows relatively rapid acceleration of the lancet structure 24 as the skin penetrating end 90 approaches and penetrates a skin cite. Portion B shows relatively slow deceleration of the lancet structure 24 as the skin penetrating end exits the skin cite. In some embodiments, a ratio of time during the extending phase to time during the retracting phase is at least about 1:25. Deceleration is adjustable by, for example, adding mass to the flywheel 351 and/or by changing the gear ratio.

Referring again to FIG. 13, as noted above, the medical diagnostic device 10 may further include the depth adjustment mechanism 37. The depth adjustment mechanism 37 may include a thumb wheel 355 that is adjustably connected to the adjustable linkage 140 at a pivot location $P_1$. Rotation of the thumb wheel 355 causes movement of an end 357 of the adjustable linkage 140, which, in turn, causes the adjustable linkage to pivot about pivot location $P_2$ and adjusts the start position of the hook portion 126 of the drive member 95. Movement of the hook portion 126 of the drive member 95 toward the lancet port 20 can increase the penetration depth of the skin penetrating end 90 of the lancet structure 24 due to the fixed stroke length of the follower arm 138 and roller wheel 186. Movement of the hook portion 126 of the drive member 95 away from the lancet port 20 can decrease the penetration depth of the skin penetrating end 90 of the lancet structure 24. As one exemplary embodiment, the penetration depth (e.g., the distance the skin penetrating end 90 extends beyond the lancet port 20) may be adjustable from about 0.8 mm to about 2.3 mm. Additionally, because the follower arm 138 is connected to the adjustable linkage 140 (e.g., at slot 381) for extending and retracting the drive member 95, the adjustable linkage 140 may act to amplify movement of the drive member 95 relative to movement of the follower arm 138. In some embodiments, the adjustable linkage 140 provides a multiplier of 1.8:1 ratio of the drive member 95 to the follower arm 138.

Figure 24:
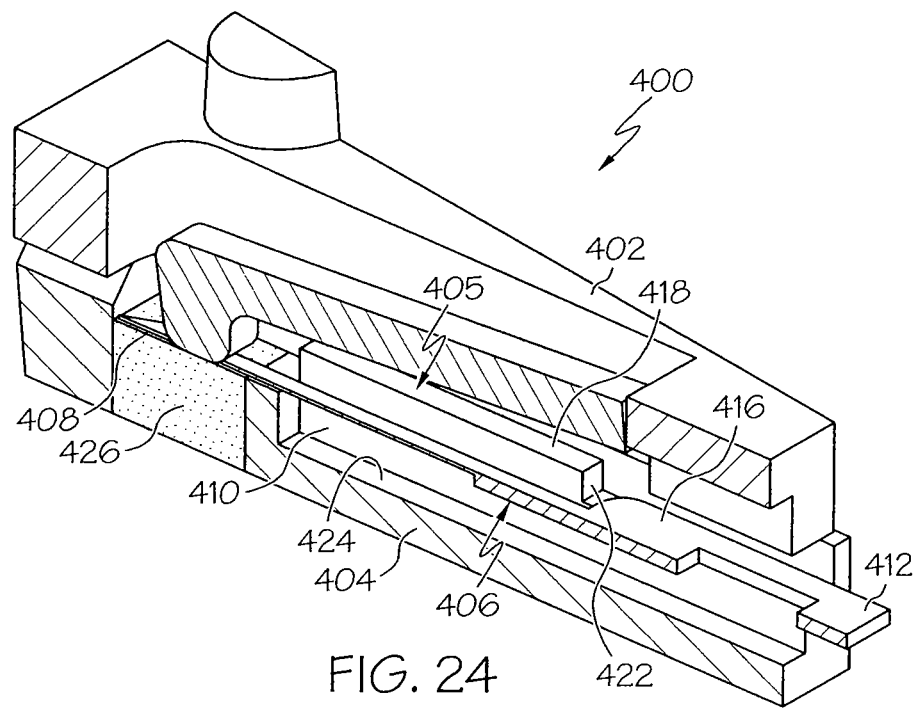
FIG. 24 illustrates another embodiment of a lancet housing assembly.

Referring now to FIG. 24, an alternative embodiment of a lancet housing assembly 400 (e.g., in the form of a disk) includes an upper disk member 402 and a lower disk member 404 defining a lancet compartment 405. A lancet structure 406 includes a skin penetrating end 408, a blood transfer portion 410 and engagement structure 412 for engaging a drive member 414. Similar to the embodiments described above, the lancet structure 406 includes a laterally extending wing 416 that can ride along a side rail 418 extending along a side wall 420 of the lancet compartment 405. In this embodiment, the side rail 418 includes a step 422 that causes the lancet structure 406 to move (i.e., snap down) toward a lancet floor 424, release the driver member and bring the skin penetrating end 408 in contact with a reagent material 426. In the illustrated embodiment, the step 422 is substantially parallel to vertical (i.e., perpendicular to the side rail 418), however, the step may be at other angles to vertical.

Figure 25:
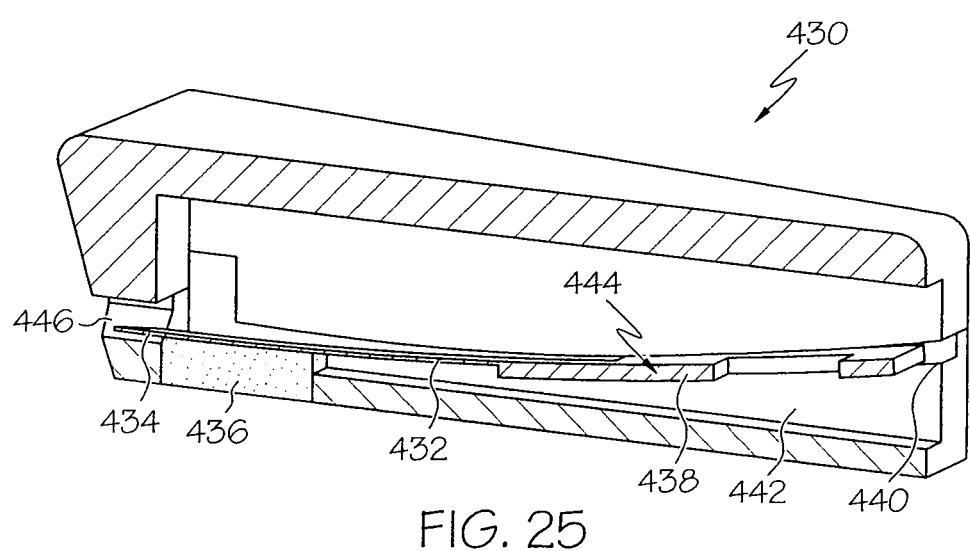
FIG. 25 illustrates another embodiment of a lancet housing assembly.

Referring to FIG. 25, another embodiment of a lancet housing assembly 430 may utilize a curvature of a lancet structure 432 to bring a skin penetrating end 434 of the lancet structure 432 in contact with a reagent material 436. In this embodiment, the lancet structure 432 includes a laterally extending wing 438 that can ride along a curved side rail 440 extending along a side wall 442 of the lancet compartment 444. When the skin penetrating end 434 is pulled by the opening 446, the curvature of the lancet structure 432 causes the skin penetrating end 434 to come into contact with the reagent material 436.

Figure 26:
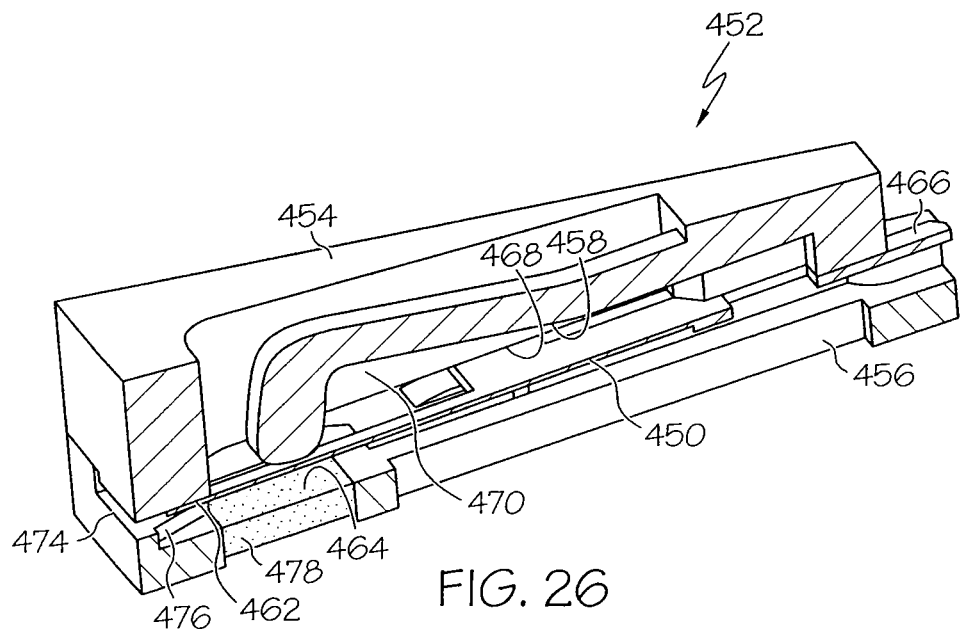
FIG. 26 illustrates another embodiment of lancet housing assembly.
Figure 27:
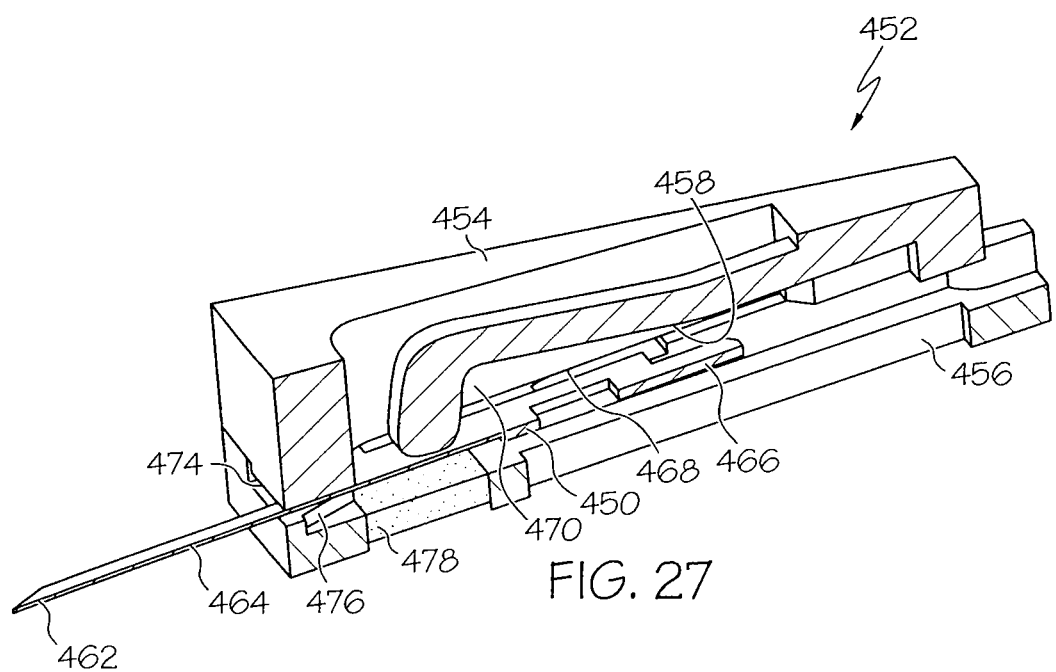
FIG. 27 illustrates the lancet housing assembly of FIG. 26 in operation.
Figure 28:
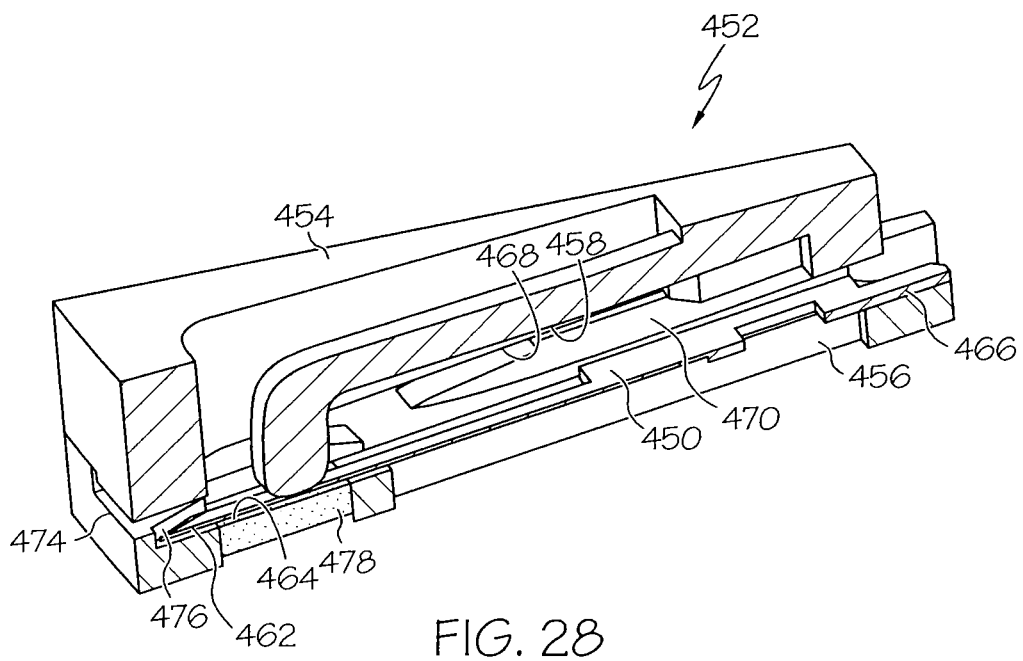
FIG. 28 illustrates the lancet housing assembly of FIG. 26 in operation.

Referring to FIGS. 26-28, movement of a lancet structure 450 may have a lateral or sideways component (i.e., angular movement toward an adjacent lancet compartment). A lancet housing assembly 452 (e.g., in the form of a disk) includes an upper disk member 454 and a lower disk member 456 defining the lancet compartment 458. The lancet structure 450 includes a skin penetrating end 462, a blood transfer portion 464 and engagement structure 466 for engaging a drive member. Similar to the embodiments described above, the lancet structure 450 includes a laterally extending wing 468 that can ride along a side rail 470 extending along a side wall 472 of the lancet compartment 458. In this embodiment, the opening 474 includes a horizontal wall component 476 that forces the skin penetrating end 462 laterally toward an adjacent lancet compartment to bring the lancet structure 450 into contact with an reagent material 478.

FIGS. 29-41 illustrate another embodiment of a lancet housing assembly 500 including an upper disk member 502 and a lower disk member 504 defining a lancet compartment 505. A lancet structure 506 includes a skin penetrating end 508, a blood transfer portion 510 and engagement structure 512 for engaging a drive member 514. Referring first to FIG. 29, securing structure 516 is provided for securing the lancet structure 506 within the lancet compartment 505. The securing structure 516 allows some force to be placed on the lancet structure 506 during engagement of the drive member 514 therewith without longitudinal displacement of the lancet structure 506. Yet, the securing structure 516 may allow for longitudinal displacement of the lancet structure 506 in response to a force above a preselected threshold force.

The securing structure 516 may include spring elements 518 and 520 that extend outwardly from the extended axis of the lancet structure 506. The spring elements 518 and 520 may each be received within a respective notch 522 and 524, which are sized to receive the spring elements 518 and 520. The locking strength of the securing structure 516 can be selected using the spring strength of the spring elements 518 and 520 and the exit angle of the notches 522 and 524. In this embodiment, the exit angles of the notches 522 and 524 are less than about 90 degrees.

FIG. 30 illustrates a starting position including the drive member 514 with the lancet structure 506 engaged with the securing structure 516. Wing structures 526 and 528 may be provided (FIG. 29) that rest upon support structures 530 to space the lancet structure 506 from a reagent material 532. The drive member 514 may be inserted into the lancet compartment 505 and pushed forwards, in a manner similar to that described above. In some embodiments, the drive member 514 is subjected to an upward spring force F (e.g., using a spring), which also is shown by FIG. 31.

In FIG. 31, the drive member 514 includes a guide projection 534 having a rounded outer periphery and extending upwardly from the hook portion 536. The guide projection 534 may engage a downwardly extending cam surface 538 to force the hook portion 536 downward to position the hook portion 536 for engagement with engagement structure 540 of the lancet structure 506. Referring to FIG. 32, as the guide projection 534 moves past the cam surface 538, the hook portion 536 raises due to the bias F and engages the engagement structure 540 of the lancet structure 506.

In FIG. 33, the spring elements 518 and 520 (FIG. 29) may free from the notches 522 and 524 and at FIG. 34, a landing member 542 may engage the cam surface 538 to limit upward movement of the hook portion 536. At FIGS. 35 and 36, an incision may be made by moving the skin penetrating end 508 through the opening 544 followed by decelerated return movement, in a fashion similar to that described above.

Figure 39:
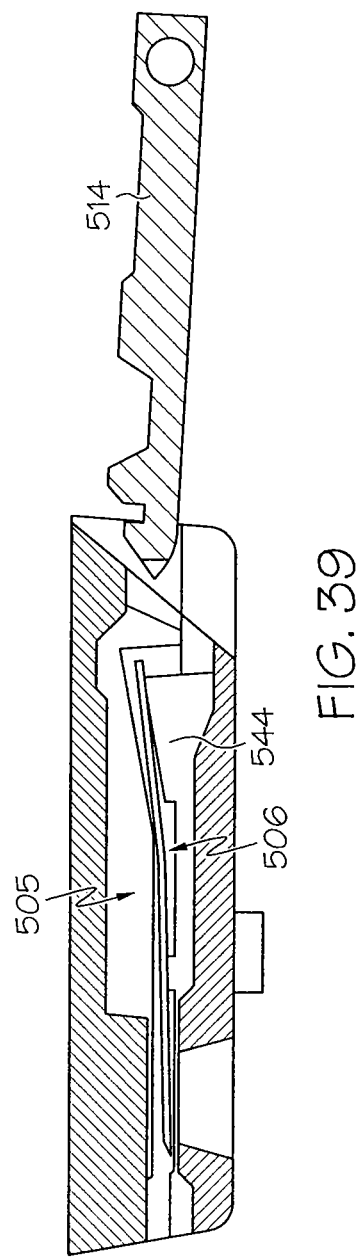
FIG. 39 illustrates the lancet housing assembly of FIG. 29 in operation.

Referring to FIG. 37, at the end of the return movement of the lancet structure 506, the bias force F acts on the lancet structure 506 thereby tensioning the lancet structure 506. With the wing structures 526 and 528 (FIG. 29) resting upon support structures 530, a gap remains between the lancet structure 506 and the reagent material 532 as shown by FIG. 37. Referring to FIG. 38, with further return movement of the drive member 514, the wing structures 526 and 528 (FIG. 29) disengage the support structures 530 and the skin penetrating end 508 contacts the reagent material 532. The bias force F facilitates contact between the skin penetrating end 508 and the reagent material 532 such that a liquid contact takes place. Upon further return of the drive member 514, the guide projection 534 engages the cam surface 538 forcing the hook portion 536 to disengage the lancet structure 506 as shown by FIG. 38. Referring to FIG. 39, ribs 544 may be provided to maintain spring tension within the lancet structure 506.

Figure 40:
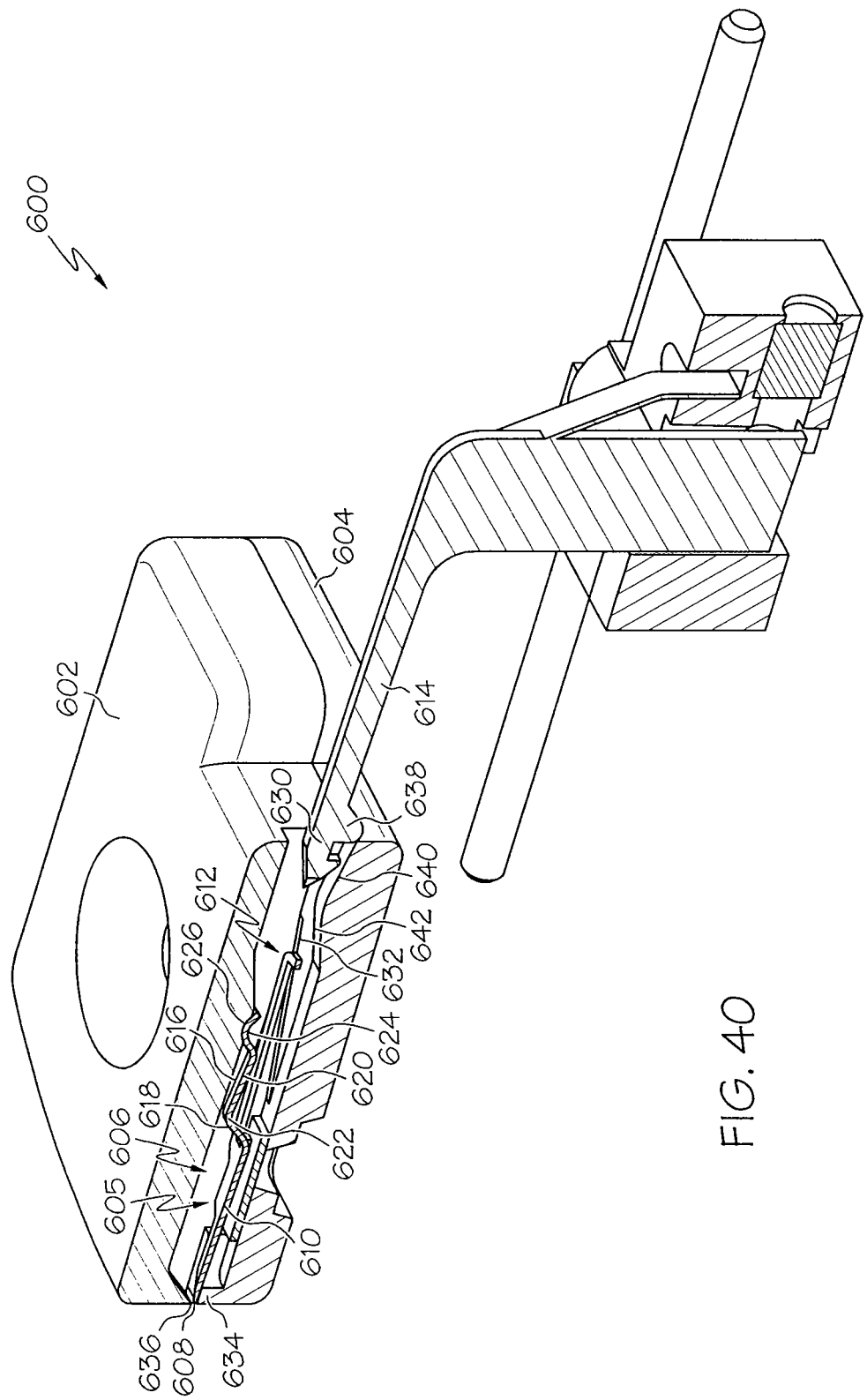
FIG. 40 illustrates another embodiment of lancet housing assembly.

FIGS. 40-47 illustrate another embodiment of a lancet housing assembly 600 including an upper disk member 602 and a lower disk member 604 defining a lancet compartment 605. A lancet structure 606 includes a skin penetrating end 608, a blood transfer portion 610 and engagement structure 612 for engaging a drive member 614. Referring first to FIG. 40, an initial position of the lancet structure 606 and the drive member 614 is illustrated. In this embodiment, the lancet structure 606 includes an outwardly extending spring finger 616 that extends upwardly at portion 618 and longitudinally at portion 620. A bend 622 connects the upwardly extending portion 618 and longitudinally extending portion 620. The longitudinally extending portion 620 includes a hump-shaped portion 624 that is received within a notch 626 thereby providing securing structure for the lancet structure 606 within the lancet compartment 605.

The lancet structure 606 includes engagement structure 612 that is used to engage the lancet structure 606 with a hook portion 630 of the drive member 614. In the illustrated initial position, the engagement structure 612 rests on a decline guide ramp or rail 632 that is used to support the lancet structure 606 during its extending and retracting phases. The skin penetrating end 608 of the lancet structure 606 rests on a support surface 634 at opening 636 through which the skin penetrating end 608 extends.

Figure 41:
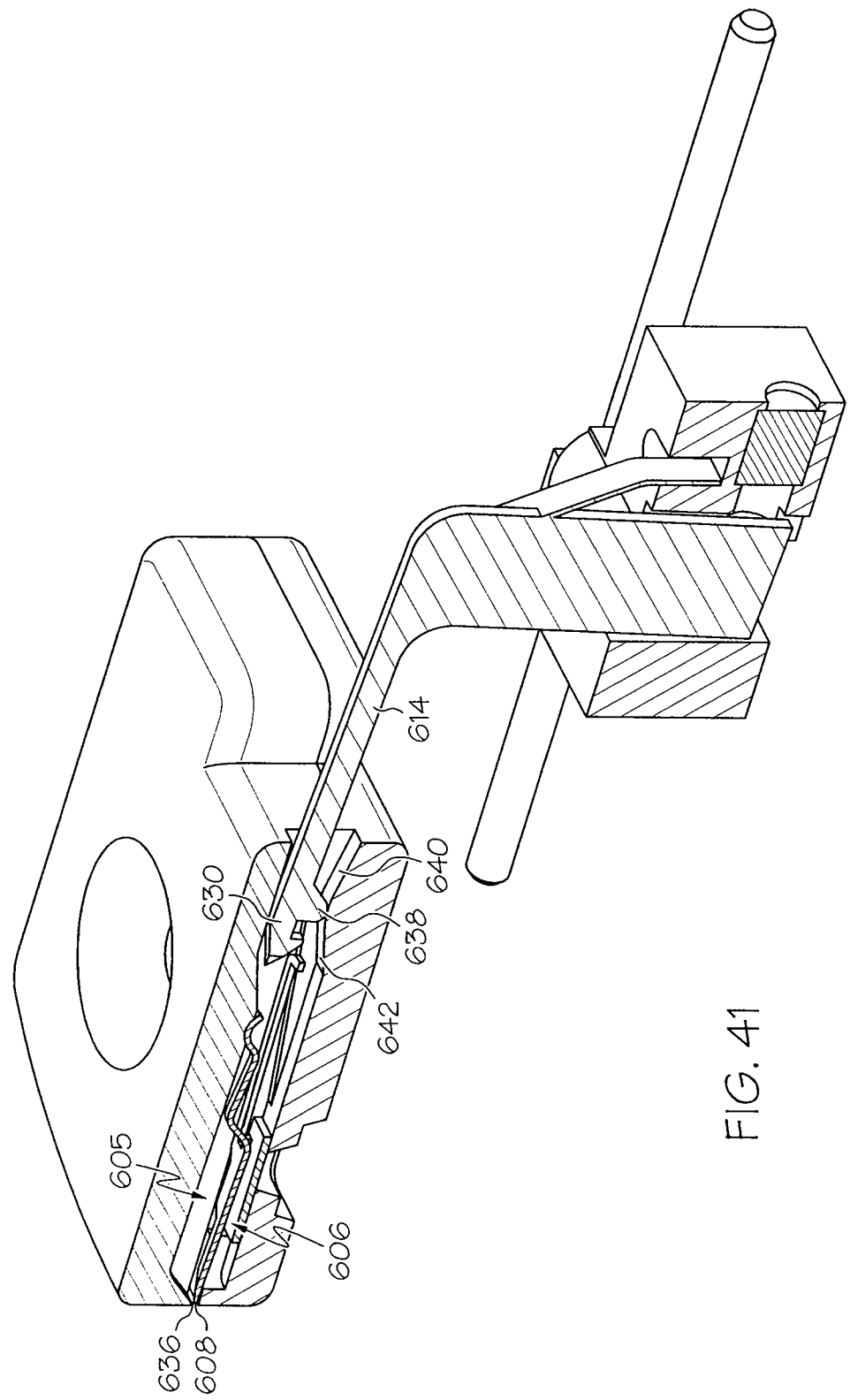
FIG. 41 illustrates the lancet housing assembly of FIG. 40 in operation.
Figure 42:
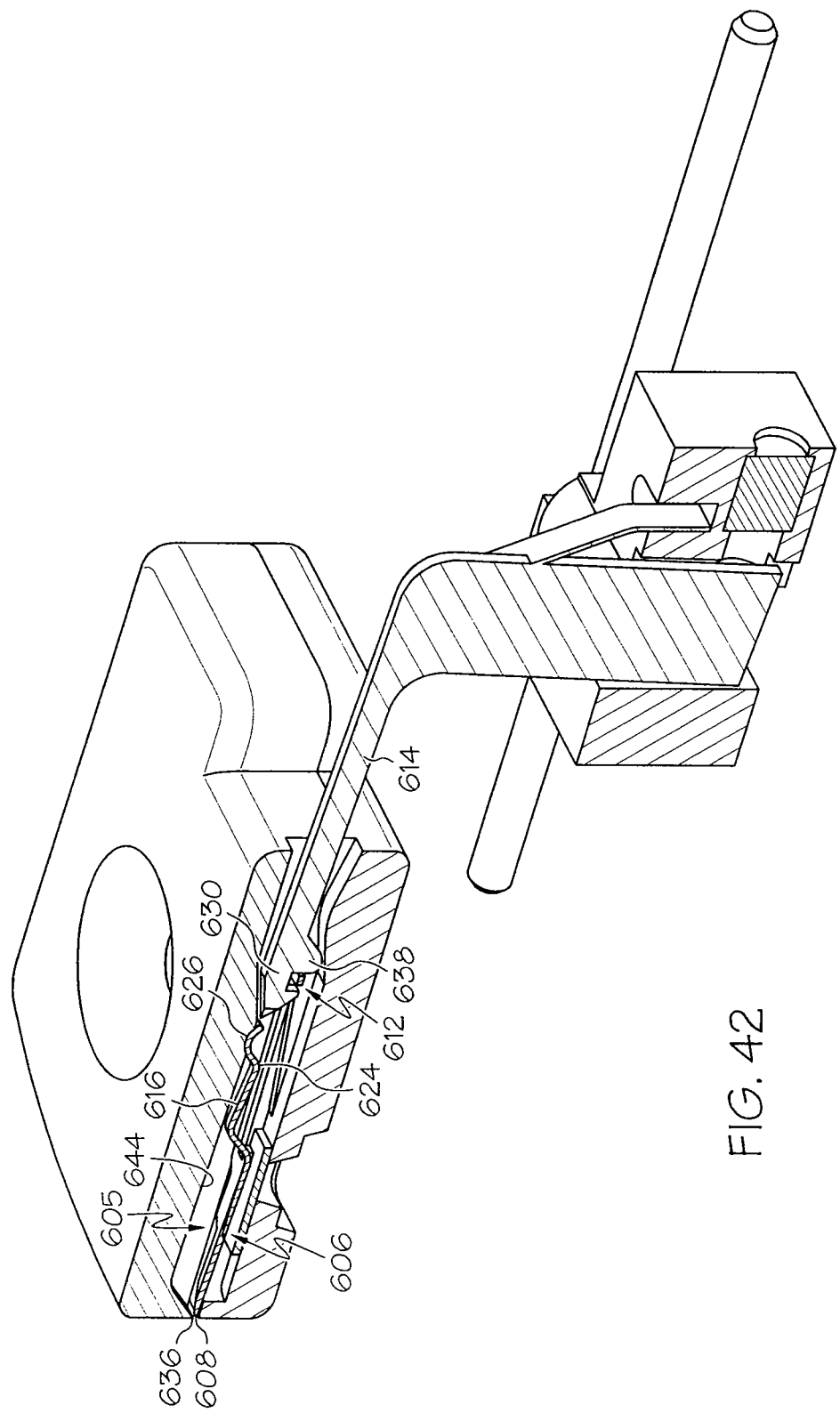
FIG. 42 illustrates the lancet housing assembly of FIG. 40 in operation.
Figure 43:
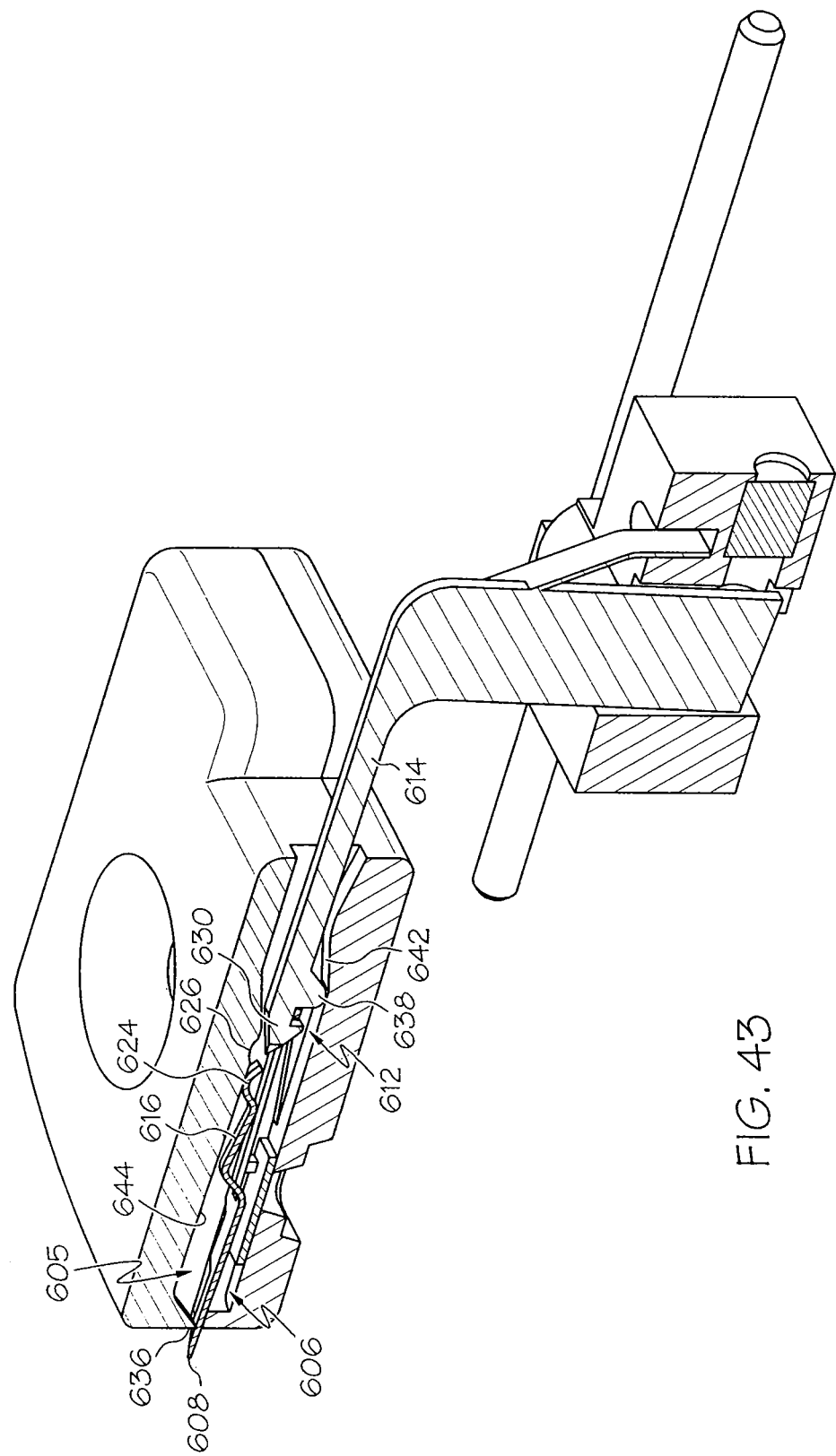
FIG. 43 illustrates the lancet housing assembly of FIG. 40 in operation.
Figure 44:
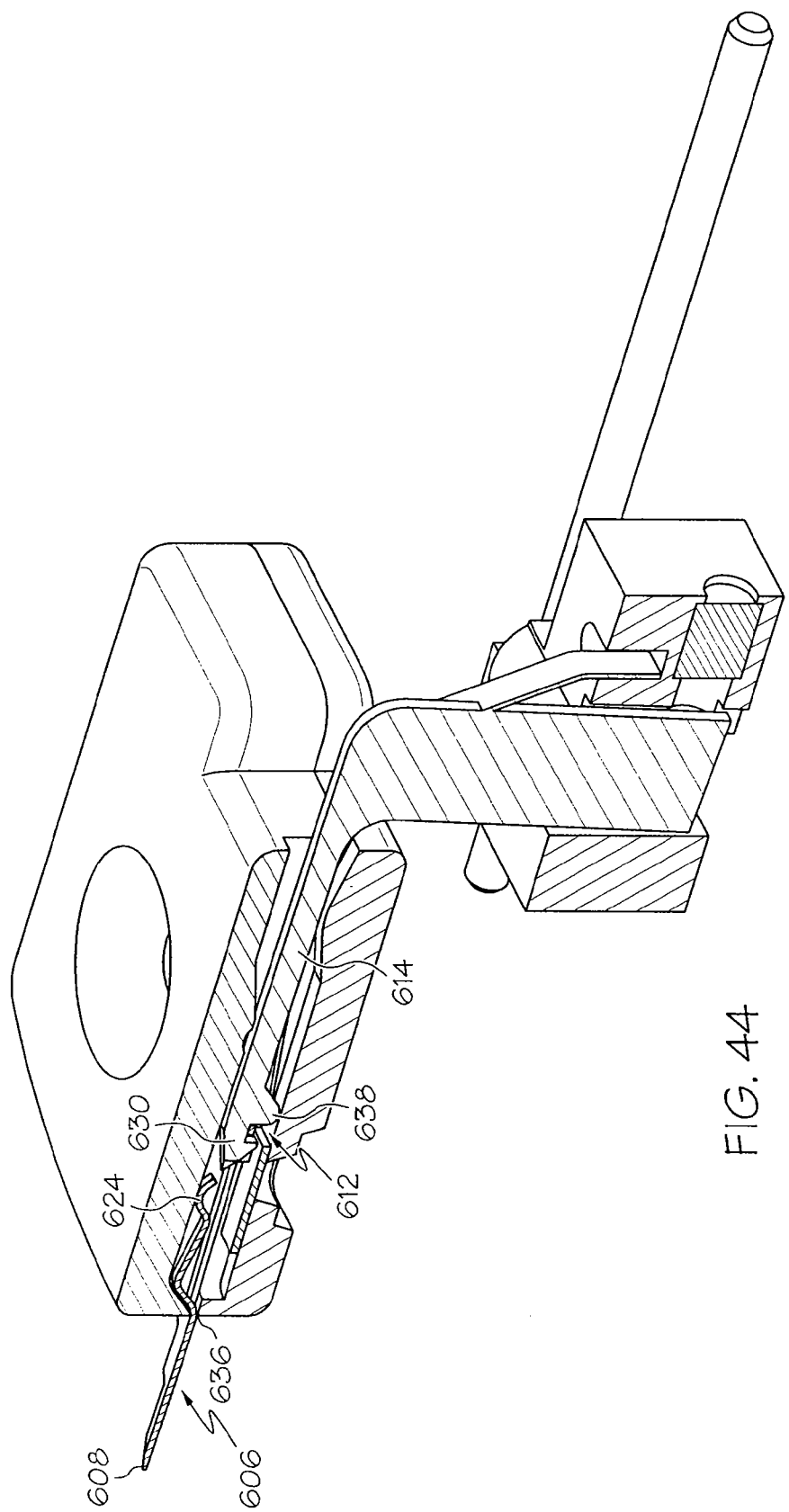
FIG. 44 illustrates the lancet housing assembly of FIG. 40 in operation.

Referring to FIG. 41, during a priming and firing sequence, the drive member 614 enters the lancet compartment 605 and a guide projection 638 engages an incline ramp surface 640, which forces the hook portion 630 upward as the drive member 614 enters the lancet compartment 605. Referring to FIG. 42, as the drive member 614 continues to move toward the opening 636, the guide projection 638 engages a decline ramp surface 642 and the hook portion 630 travels downward and engages the engagement structure 612 of the lancet structure 606. Referring to FIG. 43, the hook portion 630 continues to travel down the decline ramp surface 642 thereby fully engaging the engagement structure 612 and extending the skin penetrating end 608 of the lancet structure 606 through the opening 636. As can be seen by FIGS. 42 and 43, the hump-shaped portion 624 is forced out of the notch 626 by deflecting the spring finger 616 upon application of a sufficient force by the drive member 614. The amount of force needed to release the hump-shaped portion 624 from the notch 626 can be selected based on the spring force and the shapes of the notch 626 and hump-shaped portion 624. In some embodiments, the hump-shaped portion 624 continues to contact an upper wall surface 644 thereby biasing the lancet structure 606 in a downward direction as the skin penetrating end 608 is extended. FIG. 44 illustrates the lancet structure 606 fully extended.

Figure 45:
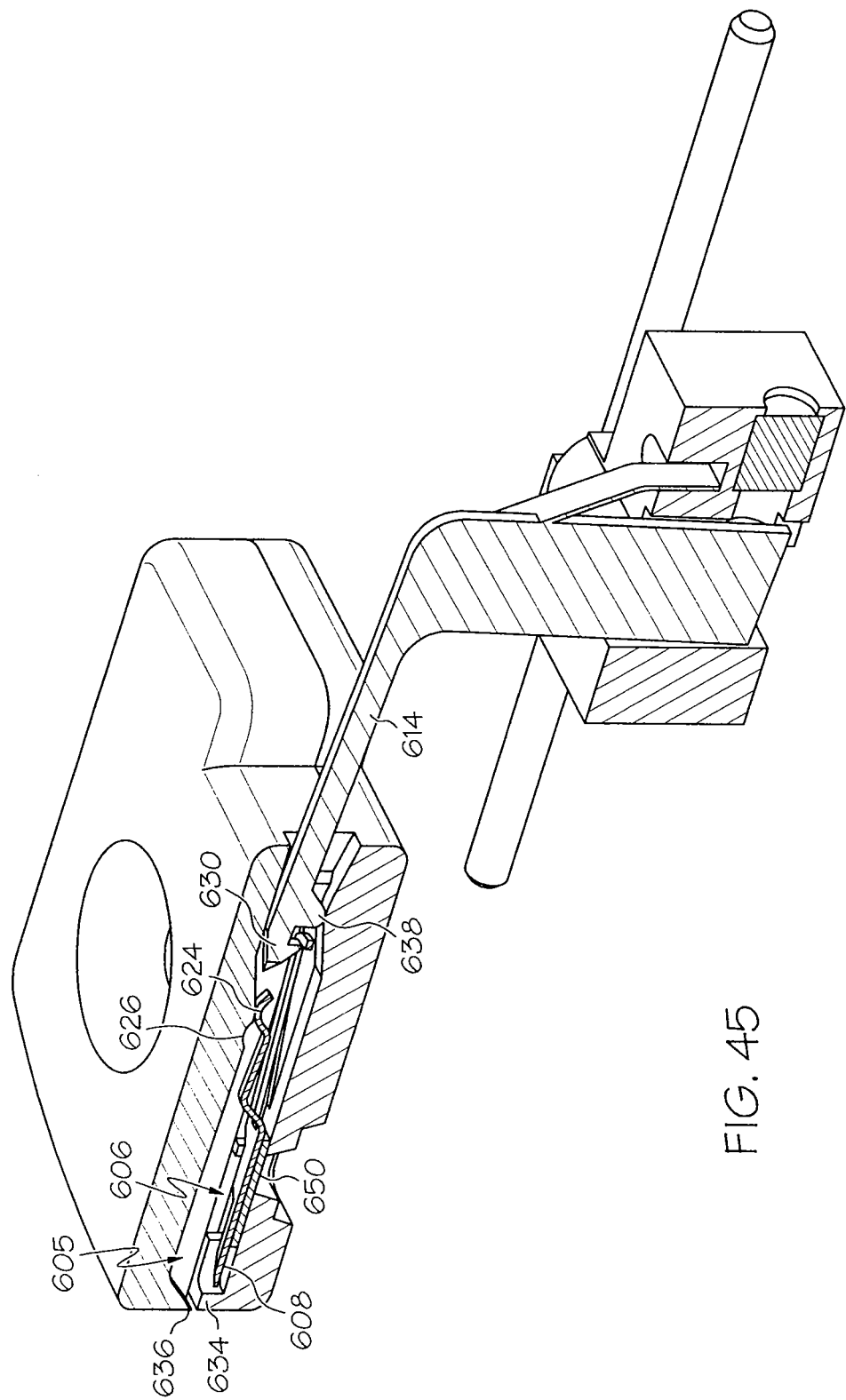
FIG. 45 illustrates the lancet housing assembly of FIG. 40 in operation.
Figure 46:
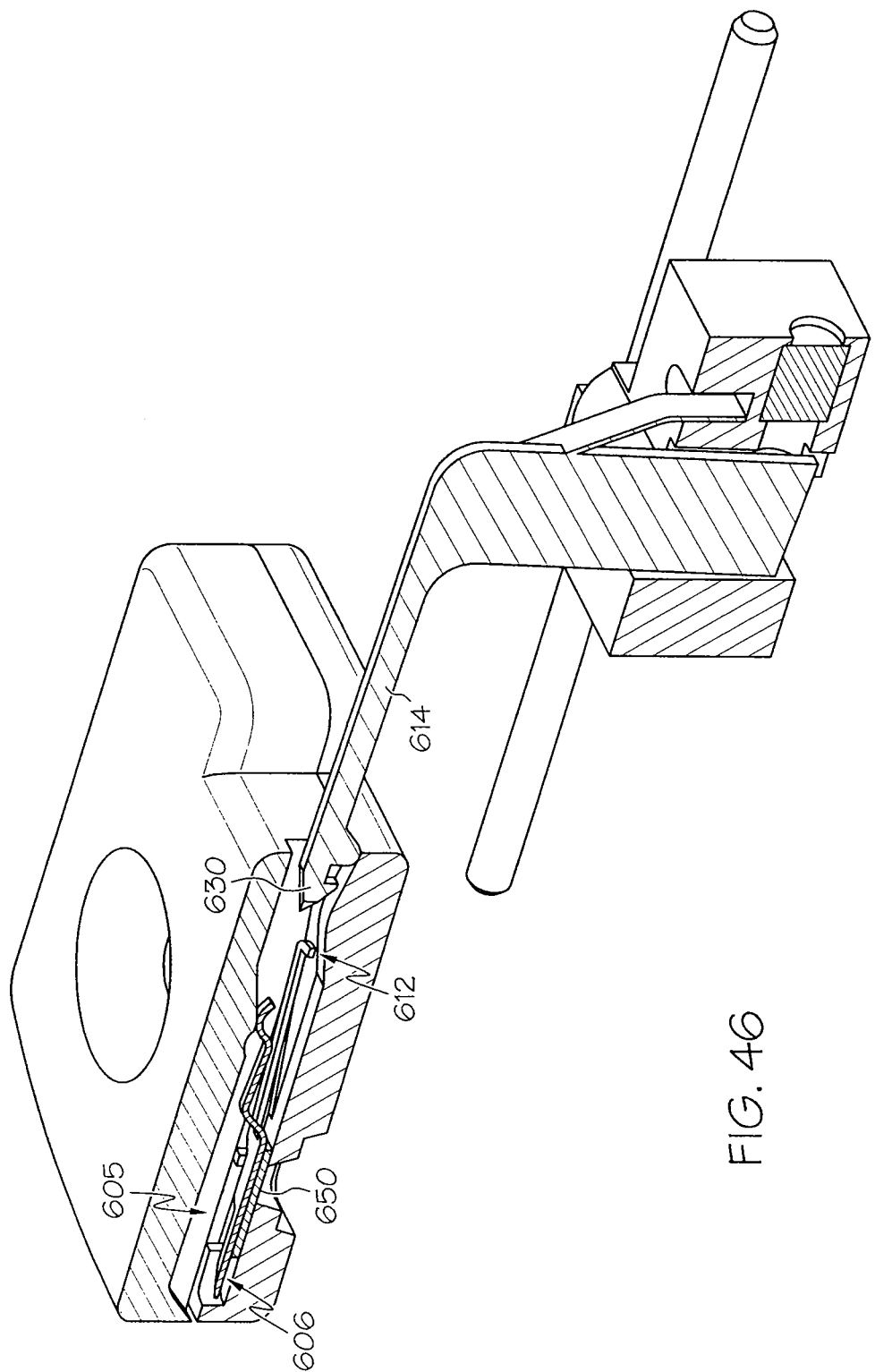
FIG. 46 illustrates the lancet housing assembly of FIG. 40 in operation.
Figure 47:
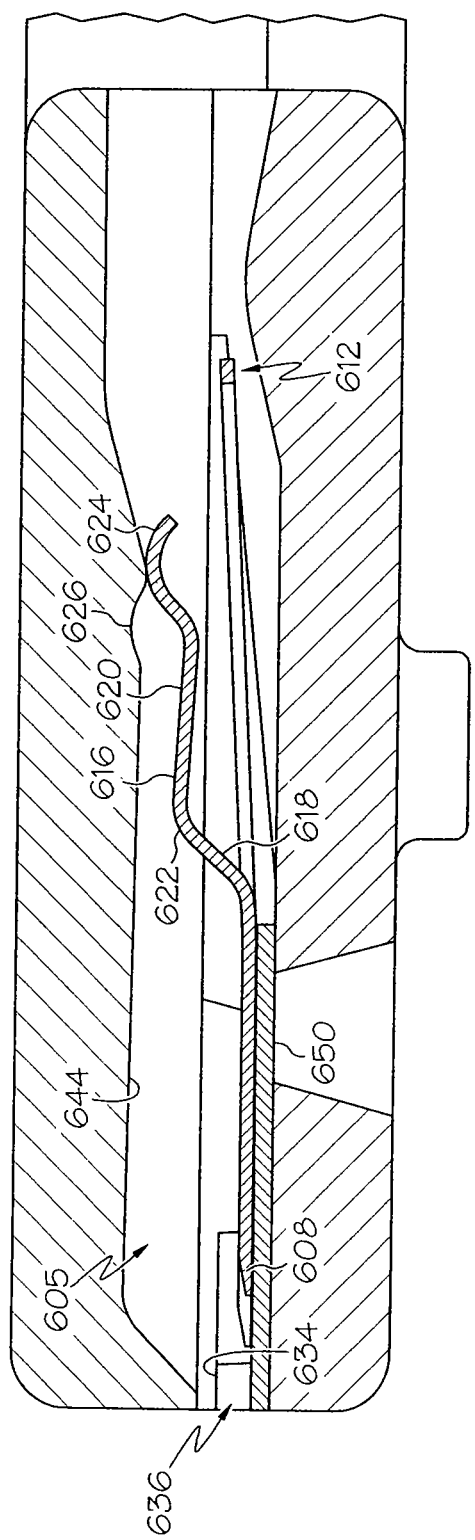
FIG. 47 illustrates the lancet housing assembly of FIG. 40 in operation.

Referring to FIG. 45, during retraction, the skin penetrating end 608 of the lancet structure 606 is pulled back into the lancet compartment 605. The pulling force applied by the drive member 614 is sufficient to pull the hump-shaped portion 624 past the notch 626 to allow the skin penetrating end 608 to clear the support surface 634 at the opening 636 and fall downward toward a reagent material 650 to transfer an amount of bodily fluid to the reagent material. Unhooking of the engagement structure 612 occurs as the lancet structure falls toward the reagent material 650 and the guide projection 638 moves up the ramp surface 642. FIGS. 46 and 47 illustrate the lancet structure 606 in its final, released state with the lancet structure 606 in contact with the reagent material 650 and the skin penetrating end 608 offset from the opening 636.

The above-described medical diagnostic devices includes a number of features that allow for improved comfort and ease of use for a patient. In general, the medical diagnostic devices may include a lancet housing assembly in the form of a cartridge or disk that is used to house multiple lancet structures for use in the medical diagnostic devices, a lancet actuator assembly for extending and retracting the lancet structures and a speed control mechanism that engages the lancet actuator assembly for adjusting the speed at which the lancet structure is extended and/or retracted by the lancet actuator assembly. A depth adjustment mechanism may also be provided that allows for adjustment of an initial position of the lancet structure prior to its use, which can adjust the penetration depth of the lancet structure during use.

The above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

What is claimed is:

1. A lancet housing assembly for use in a portable handheld medical diagnostic device for sampling bodily fluids from a skin site of a patient, the lancet housing assembly comprising:
   a housing structure comprising:
      an outer facing side;
      an inner facing side;
      an opening located at the outer facing side that is arranged and configured to align with a lancet port of the medical diagnostic device; and
      a floor that extends between the outer facing side and the inner facing side;
   a reagent material located on the floor and within the housing structure; and
   a lancet structure located in the housing structure, the lancet structure comprising a skin penetrating end aligned initially in a first plane with the opening and a blood transport portion adjacent the skin penetrating end, wherein the skin penetrating end is configured to extend in the first plane when extended through the opening and, when extended through the opening, is shaped and sized to penetrate the patient's skin at the skin site to provide an amount of blood, and further is configured to be extended and retracted by a drive member, and a biasing mechanism is configured to force the lancet structure toward the floor when the lancet is retracted to a second plane parallel to the first plane and offset from the opening, the drive member is configured to pass over the lancet structure when the drive member is moved toward the opening and the lancet structure is in the second plane, and the blood transport portion being arranged and configured to receive the amount of blood from the skin penetrating end in the second plane and to carry the amount of blood away from the skin site and to the reagent material.

2. The lancet housing assembly of claim 1, wherein the skin penetrating end of the lancet structure is supported on a bottom surface of the opening at the outer facing side before extending the skin penetrating end through the opening.

3. The lancet housing assembly of claim 1, wherein the reagent material is offset vertically from the opening at the outer face and within the housing structure.

4. The lancet housing assembly of claim 1 further comprising one or more lancet guide rails that extend along one or more of sidewalls of the at least one lancet compartment between the outer facing side and the inner facing side.

5. The lancet housing assembly of claim 4, wherein the lancet structure includes a rail riding structure providing a support surface that supports the lancet structure upon the one or more lancet guide rails.

6. The lancet housing assembly of claim 5 further comprising one or more drop down slots formed in the one or more of the sidewalls, the rail riding structure located to align with the one or more drop down slots such that the skin penetrating end is configured to move toward the reagent material when the lancet structure is retracted.

7. The lancet housing assembly of claim 1 wherein the biasing mechanism is connected at opposite ends to a ceiling of an upper disk member of the lancet housing assembly.

8. A portable handheld medical diagnostic device for sampling bodily fluids, comprising:
   a protective enclosure;
   a measurement system including a controller facilitating a physiologic measurement;
   a display device connected to the measurement system that displays information related to the physiologic measurement;
   a housing structure comprising:
      an outer facing side;
      an inner facing side;
      an opening located at the outer facing side that is arranged and configured to align with a lancet port of the medical diagnostic device; and
      a floor that extends between the outer facing side and the inner facing side;
   a reagent material located on the floor and within the housing structure; and
   a lancet structure located in the housing structure, the lancet structure comprising a skin penetrating end aligned initially in a first plane with the opening and a blood transport portion adjacent the skin penetrating end, wherein the skin penetrating end is configured to extend in the first plane when extended through the opening and, when extended through the opening, is shaped and sized to penetrate the patient's skin at the skin site to provide an amount of blood, and further is configured to be extended and retracted by a drive member, and a biasing mechanism is configured to force the lancet structure toward the floor when the lancet is retracted to a second plane parallel to the first plane and offset from the opening, the drive member is configured to pass over the lancet structure when the drive member is moved toward the opening and the lancet structure is in the second plane, and the blood transport portion being arranged and configured to receive the amount of blood from the skin penetrating end in the second plane and to carry the amount of blood away from the skin site and to the reagent material.

9. The medical diagnostic device of claim 8, wherein the skin penetrating end of the lancet structure is supported on a bottom surface of the opening at the outer facing side before extending the lancet structure.

10. The medical diagnostic device of claim 8, wherein the reagent material is offset vertically from the opening at the outer face and within the housing structure.

11. The medical diagnostic device of claim 8 further comprising one or more lancet guide rails that extend along one or more of the sidewalls between the outer facing side and the inner facing side.

12. The medical diagnostic device of claim 11, wherein the lancet structure includes a rail riding structure providing a support surface that supports the lancet structure upon the one or more lancet guide rails before extending the lancet structure.

13. The medical diagnostic device of claim 12 further comprising one or more drop down slots formed in the one or more of the sidewalls, the rail riding structure located to align with the one or more drop down slots such that the skin penetrating end is configured to move toward the reagent material.

14. The medical diagnostic device of claim 8 further comprising a motor operatively connected to the lancet structure.

15. A method of controlling movement of a lancet structure provided within a lancet housing assembly in a portable handheld medical diagnostic device for sampling bodily fluids from a skin site of a patient, the method comprising:
providing a lancet structure located the lancet housing assembly, wherein the lancet housing assembly is configured to have an outer facing side and an opening located at the outer facing side that is arranged and configured to align with a lancet port of the medical diagnostic device, the lancet structure comprising a skin penetrating end aligned initially in a first plane with the opening and a blood transport portion adjacent the skin penetrating end, wherein the skin penetrating end is configured to extend in the first plane when extended through the opening and, when extended through the opening, is shaped and sized to penetrate the patient's skin at the skin site to provide an amount of blood, and further is configured to be extended and retracted by a drive member, and a biasing mechanism is configured to force the lancet structure toward a lancet floor when the lancet is retracted to a second plane parallel to the first plane and offset from the opening, the drive member is configured to pass over the lancet structure when the drive member is moved toward the opening and the lancet structure is in the second plane, and the blood transport portion being arranged and configured to receive the amount of blood from the skin penetrating end in the second plane and to carry the amount of blood away from the skin site and to a reagent material located on the floor within the at least one lancet compartment;
extending the skin penetrating end through a port of the medical diagnostic device and
penetrating the patient's skin at the skin site to provide an amount of blood; receiving the amount of blood at the skin penetrating end; and
carrying the amount of blood away from the skin site to the reagent material using the blood transport portion.

16. The method of claim 15 comprising supporting the skin penetrating end of the lancet structure on a bottom surface at the port with the lancet structure before extending the skin penetrating end.

17. The method of claim 15 further comprising providing a reagent material offset vertically from the port within the lancet compartment.

18. The method of claim 15 further comprising connecting a motor to the lancet structure.

* * * * *